US007476387B2

(12) United States Patent
Aguirre et al.

(10) Patent No.: US 7,476,387 B2
(45) Date of Patent: Jan. 13, 2009

(54) CHIMERIC EMPTY VIRAL-LIKE PARTICLES DERIVED FROM THE INFECTIOUS BURSAL DISEASE VIRUS (IBDV), PROCESS FOR THEIR PRODUCTION AND APPLICATIONS

(75) Inventors: Jose Francisco Rodriguez Aguirre, Madrid (ES); Jose Ruiz Caston, Madrid (ES); Irene Saugar Gomez, Madrid (ES); Ana Maria Ona Blanco, Madrid (ES); Juan Ramon Rodriguez Fernandez-Alba, Madrid (ES)

(73) Assignee: Chimera Pharma S.L.U., Madrid (ES)

( * ) Notice: Subject to any disclaimer, the term of this patent is extended or adjusted under 35 U.S.C. 154(b) by 0 days.

(21) Appl. No.: 11/433,847

(22) Filed: May 11, 2006

(65) Prior Publication Data

US 2007/0015243 A1 Jan. 18, 2007

(30) Foreign Application Priority Data

Jul. 15, 2005 (ES) ................................ 200501733

(51) Int. Cl.
*A61K 39/12* (2006.01)
*A61K 39/385* (2006.01)
*C12P 21/02* (2006.01)
*C07K 19/00* (2006.01)
*C07K 14/08* (2006.01)

(52) U.S. Cl. .................. 424/192.1; 530/350; 435/69.7; 435/235.1

(58) Field of Classification Search ................ 435/69.1, 435/456; 424/208.1, 199.1
See application file for complete search history.

(56) References Cited

U.S. PATENT DOCUMENTS

| 5,290,686 | A  | 3/1994  | Kendal et al.    |
| 5,605,792 | A  | 2/1997  | Jackwood et al.  |
| 5,605,827 | A  | 2/1997  | Jackwood et al.  |
| 5,614,409 | A  | 3/1997  | Azad et al.      |
| 5,616,327 | A  | 4/1997  | Judd et al.      |
| 5,641,490 | A  | 6/1997  | Paoletti et al.  |
| 5,658,572 | A  | 8/1997  | Paoletti et al.  |
| 5,788,970 | A  | 8/1998  | Vakharia et al.  |
| 5,871,744 | A  | 2/1999  | Vakharia et al.  |
| 5,916,879 | A  | 6/1999  | Webster          |
| 5,932,426 | A  | 8/1999  | Baralle et al.   |
| 6,017,759 | A  | 1/2000  | Vakharia et al.  |
| 6,114,112 | A  | 9/2000  | Jackwood         |
| 6,156,314 | A  | 12/2000 | Vakharia et al.  |
| 6,169,175 | B1 | 1/2001  | Frace et al.     |
| 6,231,868 | B1 | 5/2001  | Vakharia et al.  |
| 6,274,147 | B1 | 8/2001  | Vakharia et al.  |
| 6,406,843 | B1 | 6/2002  | Skeeles et al.   |
| 6,458,362 | B1 | 10/2002 | Casal et al.     |
| 6,528,063 | B2 | 3/2003  | Stram et al.     |
| 6,596,280 | B1 | 7/2003  | Vakharia et al.  |
| 6,602,705 | B1 | 8/2003  | Barnett et al.   |
| 6,764,684 | B2 | 7/2004  | Saitoh et al.    |
| 6,872,395 | B2 | 3/2005  | Kawaoka          |
| 6,936,256 | B2 | 8/2005  | Vakharia         |
| 6,964,769 | B2 | 11/2005 | Sebbel et al.    |
| 7,022,327 | B1 | 4/2006  | Lütticken et al. |
| 2002/0081295 | A1* | 6/2002 | Schiller et al. ........... 424/143.1 |
| 2002/0165176 | A1 | 11/2002 | Haynes et al.   |
| 2003/0054010 | A1* | 3/2003 | Sebbel et al. ............ 424/185.1 |
| 2003/0152592 | A1 | 8/2003  | Boot et al.      |
| 2003/0175301 | A1 | 9/2003  | Cohen et al.     |
| 2004/0005338 | A1 | 1/2004  | Bachmann et al. |
| 2004/0116664 | A1 | 6/2004  | De Filette et al. |
| 2004/0223976 | A1 | 11/2004 | Bianchi et al.  |
| 2005/0003349 | A1 | 1/2005  | Kawaoka          |
| 2005/0009008 | A1 | 1/2005  | Robinson et al. |
| 2005/0186621 | A1 | 8/2005  | Galarza et al.  |
| 2006/0024670 | A1 | 2/2006  | Luke et al.      |
| 2006/0121468 | A1 | 6/2006  | Allnutt et al.  |
| 2006/0121567 | A1 | 6/2006  | Vakharia         |
| 2006/0251623 | A1 | 11/2006 | Bachmann et al. |

FOREIGN PATENT DOCUMENTS

| EP | 0 861 665 A1 | 9/1998  |
| EP | 0 887 412 B1 | 12/1998 |
| EP | 1 069 187 A1 | 1/2001  |
| EP | 1 621 612 A1 | 2/2006  |
| JP | 5194597 A    | 8/1993  |

(Continued)

OTHER PUBLICATIONS

Boot et al., "Rescue of Very Virulent and Mosaic Infectious Bursal Disease Virus from Cloned cDNA: VP2 is not the Sole Determinant of the Very Virulent Phenotype," Journal of Virology, vol. 74, No. 15, pp. 6701-6711 (2000).*

(Continued)

*Primary Examiner*—Mary E Mosher
(74) *Attorney, Agent, or Firm*—Klarquist Sparkman, LLP

(57) ABSTRACT

The chimeric empty viral-like particles derived from the infectious bursal disease virus (IBDV) are formed by the assembly of fusion proteins comprising a region A consisting of an IBDV pVP2 protein or a "1-n" fragment of said IBDV pVP2, wherein "n" is an integer comprised between 441 and 501, bound to a region B consisting of a heterologous polypeptide comprising a polypeptide of interest, such as a polypeptide useful for prophylactic, therapeutic or diagnostic purposes.

25 Claims, 11 Drawing Sheets

FOREIGN PATENT DOCUMENTS

| | | |
|---|---|---|
| WO | WO 93/03145 A1 | 2/1993 |
| WO | WO 95/26196 A1 | 10/1995 |
| WO | WO 98/09646 A1 | 3/1998 |
| WO | WO 98/33522 A1 | 8/1998 |
| WO | WO 98/50071 A1 | 11/1998 |
| WO | WO 99/16866 A1 | 4/1999 |
| WO | WO 00/37649 A2 | 6/2000 |
| WO | WO 01/97839 A1 | 12/2001 |
| WO | WO 02/00885 A2 | 1/2002 |
| WO | WO 02/088339 | 11/2002 |
| WO | WO 02/096940 A2 | 12/2002 |
| WO | WO 03/013597 A1 | 2/2003 |
| WO | WO 03/024480 A2 | 3/2003 |
| WO | WO 03/024481 A2 | 3/2003 |
| WO | WO 03/074552 A1 | 9/2003 |
| WO | WO 2004/003143 A2 | 1/2004 |
| WO | WO 2004/007538 A2 | 1/2004 |
| WO | WO 2004/025263 A2 | 3/2004 |
| WO | WO 2004/087900 A1 | 10/2004 |
| WO | WO 2005/049794 A2 | 6/2005 |
| WO | WO 2005/071068 A1 | 8/2005 |
| WO | WO 2005/071069 A1 | 8/2005 |
| WO | WO 2005/105834 A1 | 11/2005 |
| WO | WO 2006/027698 A1 | 3/2006 |
| WO | WO 2006/032674 A1 | 3/2006 |

OTHER PUBLICATIONS

Heine et al (Virus Research 32:313-328, 1994).*
Wang et al (Biotechnology and Bioengineering 67:104-111, 2000).*
Coulibaly et al. Cell 120:761-772, Mar. 25, 1005.*
Birghan et al., "A non-canonical Ion proteinase lacking the ATPase domain employs the Ser-Lys catalytic dyad to exercise broad control over the life cycle of a double-stranded RNA virus," Embo J., 19:114-123, 2000.
Böttcher et al., "Three-dimensional structure of infectious bursal disease virus determined by electron cryomicroscopy," J. Virol., 71:325-330, 1997.
Castón et al., "C terminus of infectious bursal disease virus major capsid protein VP2 is involved in definition of the T number for capsid assembly," J. Virol., 75:10815-10828, 2001.
Chevalier et al., "The maturation process of pVP2 requires assembly of infectious bursal disease virus capsids," J. Virol., 76:2384-2392, 2002.
Chevalier et al., "The last C-terminal residue of VP3, glutamic acid 257, controls capsid assembly of infectious bursal disease virus," J. Virol., 78:3296-3303, 2004.
Chung et al., "Sequence analysis of the bicistronic Drosophila X virus genome segment A and its encoded polypeptides," Virology, 225:359-368, 1996.
Da Costa et al., "The capsid of infectious bursal disease virus contains several small peptides arising from the maturation process of pVP2," J. Virol., 76:2393-2402, 2002.
Da Costa et al., "Blotched snakehead virus is a new aquatic birnavirus that is slightly more related to avibirnavirus than to aquabirnavirus," J. Virol., 77:719-725, 2003.
Fernández-Arias et al., "Expression of ORF A1 of infectious bursal disease virus results in the formation of virus-like particles," J. Gen. Virol., 79:1047-1054, 1998.
Fernández-Arias et al., "The major antigenic protein of infectious bursal disease virus, VP2, is an apoptotic inducer," J. Virol., 71:8014-8018, 1997.
Galarza et al., "Virus-like particle (VLP) vaccine conferred complete protection against a lethal influenza virus challenge," Viral. Immunol., 18:365-372, 2005.
Hu et al., "Chimeric infectious bursal disease virus-like particles expressed in insect cells and purified by immobilized metal affinity chromatography," Biotechnol. Bioeng., 63:721-729, 1999.
Hu and Bentley, "Effect of MOI ratio on the composition and yield of chimeric infectious bursal disease virus-like particles by baculovirus co-infection: deterministic predictions and experimental results," Biotechnol. Bioeng. 75:104-119, 2001.
Ionescu et al., "Pharmaceutical and immunological evaluation of human papillomavirus viruslike particle as an antigen carrier," J. Pharm. Sci., 95:70-79, 2006.
Jagadish et al., "Expression and characterization of infectious bursal disease virus polyprotein in yeast," Gene, 95:179-186, 1990.
Jegerlehner et al., "Influenza A vaccine based on the extracellular domain of M2: weak protection mediated via antibody-dependent NK cell activity," J. Immunol. 172:5598-5605, 2004.
Kadono-Okuda et al., "Baculovirus-mediated production of the human growth hormone in larvae of the silkworm Bombyx mori." Biochem. Biophys. Res. Commun., 213:389-396, 1995.
Katagiri and Ingham, "Enhanced production of green fluorescent fusion proteins in baculovirus expression system by addition of secretion signal," Biotechniques, 33:24-26, 2002.
Kibenge et al., "Formation of virus-like particles when the polyprotein gene (segment A) of infectious bursal disease virus is expressed in insect cells," Can. J. Vet. Res., 63:49-55, 1999.
Kingsman et al., "Yeast retrotransposon particles as antigen delivery systems," Ann. N. Y. Acad. Sci., 754:202-213, 1995.
Kochan et al., "Characterization of the RNA binding activity of VP3, a major structrual protein of IBDV," Arch. Virol., 148:723-744, 2003.
Lejal et al., "Role of Ser-652 and Lys-692 in the protease activity of infectious bursal disease virus VP4 and identification of its substrate cleavage sites," J. Gen. Virol., 81:983-992, 2000.
Leong et al. (Eds.), "Virus TaxonomyThe Classification and Nomenclature of Viruses: Seventh Report of International Committee on Taxonomy of Viruses," Academic Press, San Diego, pp. 481-490, 2000.
Leusch et al., "A novel host-vector system for direct selection of recombinant baculoviruses (bacmids) in Escherichia coli.," Gene, 160:191-194, 1995.
Lo-Man, et al., "A recombinant virus-like particle system derived from parvoviruses as an efficient antigen carrier to elicit a polarized Th1 immune response without adjuvant," Eur. J. Immunol., 28:1401-1407, 1998.
Lombardo et al., "VP1, the putative RNA-dependent RNA polymerase of infectious bursal disease virus, forms complexes with the capsid protein VP3, leading to efficient encapsidation into virus-like particles," J. Virol., 73:6973-6983, 1999.
Lombardo et al., "VP5, the nonstructural polypeptide of infectious bursal disease virus, accumulates within the host plasma membrane and induces cell lysis," Virology, 277:345-357, 2000.
Luckow et al., "Efficient generation of infectious recombinant baculoviruses by site-specific tranposon-mediated insertion of foreign genes into a baculovirus genome propagated in Escherichia coli.," J. Virol., 67:4566-4579, 1993.
Macreadie et al., "Passive protection against infectious bursal disease virus by viral VP2 expressed in yeast," Vaccine, 8:549-552, 1990.
Maraver et al., "Indentification and molecular characterization of the RNA polymerase-binding motif of the inner capsid protein VP3 of infectious bursal disease virus," J. Virol., 77:2459-2468, 2003
Maraver et al., "The Oligomerization Domain of VP3, the Scaffolding Protein of Infectious Bursal Disease Virus, Plays a Critical Role in Capsid Assembly," J. Virol., 77:6438-6449, 2003.
Martínez-Torrecuadrada et al., "Different architectures in the assembly of infectious bursal disease capsid protien expressed in insect cells," Virology, 278:322-331, 2000.
Martínez-Torrecuadrada et al., "Structure-dependent efficacy of infectious bursal disease virus (IBDV) recombinant vaccines," Vaccine, 21:3342-3350, 2003.
Oña et al., "The C-terminal domain of the pVP2 precursor is essential for the interaction between VP2 and VP3, the capsid polypeptides of infectious bursal disease virus," *Virology*, 322:135-142, 2004.
Pitcovski et al., "Development and large-scale use of recombinant VP2 vaccine for the prevention of infectious bursal disease of chickens," *Vaccine*, 21:4736-4743, 2003.
Pous et al., "Structure of birnavirus-like particles determined by combined electorn cryomicroscopy and X-ray crystallography," *J. Gen. Virol.*, 86:2339-2346, 2005.

Qiu et al., "Expression and characterization of virus-like particles containing rubella virus structual protein," *J. Virol.*, 68:4086-4091, 1994.

Razzini et al., "Low-density lipoprotien (LDL) receptor/transferrin fusion protein: in vivo production and functional evaluation as a potential therapeutic tool for lowering plasma LDL cholesterol.," *Hum. Gene Ther.*, 15:533-541, 2004.

Sánchez and Rodriíguez, "Proteolytic processing in infectious bursal disease virus: identification of the polyprotein cleavage sites by site-directed mutagenesis," *Virology*, 262:190-199, 1999.

Schmidt et al., "Binding of external ligands onto an engineered virus capsid.," *Protein Eng.*, 14:769-774, 2001.

Sharma et al., "Infectious bursal disease virus of chickens: pathogenesis and immunosuppression," *Dev. Comp. Immunol.*, 24:223-235, 2000.

Shin and Folk, "Formation of polyomavirus-like particles with different infectious bursal disease virus, play a critical role for capsid formation," *J. Virol.*, 77:11491-11498, 2003.

Shivappa et al., "Development of a subunit vaccine for infectious pancreatic necrosis virus using a baculovirus insect/larvae system," *Dev. Biol. (Basel)*, 121:165-174, 205.

Tacken et al., "Interactions in vivo between the proteins of infectious bursal disease virus: capsid protein VP3 intereacts with the RNA-dependent RNA polymerase, VP1," *J. Gen. Virol.*, 81:209-218, 2000.

Vakharia et al., "Infectious bursal disease virus structural proteins expressed in a baculovirus recombinant confer protection in chickens," *J. Gen. Virol.*, 74:1201-1206, 1993.

Vakharia, "Development of recombinant vaccines against infectious bursal disease," *Biotechnol. Ann. Rev.*, 3:151-168, 1997.

Van Den Berg et al., "Infectious bursal disease (Gumboro disease)," *Rev. Sci. Tech.*, 19:527-543, 2000.

Veenendaal et al., "In vitro and in vivo studies of $VEGF_{121}$/rGelonin chimeric fusion toxin targeting the neovasculature of solid tumors," *Proc. Natl. Acad. Sci. U.S.A.*, 99:7866-7871, 2002.

Wang et al., "Self-assembly of the infectious bursal disease virus capsid protein, rVP2, expressed in insect cells and purification of immunogenic chimeric rVP2H particles by immobilized metal-ion affinity chromatography," *Biotechnol. Bioeng.* 67:104-111, 2000.

Yao and Vakharia, "Generation of infectious pancreatic necrosis virus from cloned cDNA," *J. Virol.*, 72:8913-8920, 1998.

\* cited by examiner

pESCURA/pVP2-456-BT Sucrose gradient 15-40%

Bottom → Top

F6 F7 F8 F9 F10 F11 pESCURA/pVP2 anti-VP2 anti-FMDV

FIGURE 11

CHIMERIC EMPTY VIRAL-LIKE PARTICLES DERIVED FROM THE INFECTIOUS BURSAL DISEASE VIRUS (IBDV), PROCESS FOR THEIR PRODUCTION AND APPLICATIONS

CROSS-REFERENCE TO RELATED APPLICATIONS

This application claims benefit under 35 U.S.C. § 119 of Spanish Patent Application No. P200501733, filed on Jul. 15, 2005, the disclosure of which is incorporated herein for all purposes.

FIELD OF THE INVENTION

The invention is related to producing chimeric empty viral-like particles derived from the infectious bursal disease virus (IBDV) and its applications.

BACKGROUND OF THE INVENTION

Viral-like particles are structures specialized in packaging and carrying nucleic acids and proteins. A general characteristic of viral-like particles is their excellent ability to stimulate the host's immune response. These properties make viral-like particles extremely interesting agents for developing intracell delivery systems and for generating sub-unit vaccines. The use of different gene expression systems has aided in producing empty viral capsids or viral-like particles (VLPs) of several viruses, for example rotavirus (US 2003/0175301), retrovirus (U.S. Pat. No. 6,602,705), parvovirus (U.S. Pat. No. 6,458,362), etc. The genetic manipulation of these expression systems in turn allows producing VLPs containing heterologous amino acid sequences from proteins different from those forming the native viral capsid. These VLPs are generically called heterotypical, recombinant or chimeric VLPs (CV-LPs), and they have mainly been used for two purposes: (i) generating multivalent vaccines by means of immunogenetically relevant heterologous peptides, and (ii) modifying tropism, by means of inserting amino acid sequences involved in receptor-ligand interactions.

The infectious bursal disease virus (IBDV), which belongs to the Birnaviridae family, infects several avian species and is directly responsible for infectious bursitis, a severe immuno-suppressive disease causing considerable economic losses in the avian industry worldwide.

IBDV particles are icosahedral with symmetry T=13, they lack the envelope and are formed by a single protein layer. Until now, the approaches aimed at obtaining an atomic model for IBDV particles have failed. For this reason, the available information on their structure is based on three-dimensional models generated from images obtained by electron cryomicroscopy of the purified virus and VLPs. Based on these studies, it has been observed that the outer surface of the particle is formed by a continuous lattice of 260 trimers of protein VP2 (37 kDa) arranged in five different conformations. The inner side of the particles contains 200 trimers of protein VP3 (29 kDa), the latter ones, independently of one another, are bound to the basal area of the VP2 trimers. It has been suggested that a third polypeptide, VP4 (28 kDa), could also be part of the particles, being located at the base of the pentamers forming the angles of the icosahedral structure.

Polypeptides VP2, VP3 and VP4 are produced from proteolytic processing of a precursor polypeptide with a size of 109 kDa. This precursor is auto-catalytically processed, releasing the polypeptides pVP2 (48 kDa), VP3 and VP4. The VP4 domain, which is located in the central region of the polyprotein, belongs to the family of Ion proteases and is responsible for the proteolytic cut. Polypeptides pVP2 and VP3 are directly responsible for assembling the capsids. The pVP2 product suffers a last cut at its C-terminal end before giving rise to the mature form of the protein, VP2, which is the form found in the purified particles. This pVP2 processing is necessary for correctly forming the capsids and it requires the presence of VP3, although the protease responsible has not yet been identified.

Morphogenesis is a vital process for the viral cycle requiring successive steps associated to modifications in precursor polypeptides. As a result, viruses have developed strategies allowing the sequential and correct interaction between each one of their components. One of these strategies, frequently used by icosahedral viruses, consists of the use of polypeptides of a single polyprotein as the basis of their structural components. In these cases, correct proteolytic processing of said polyprotein plays a crucial role in the assembly process.

This principle for IBDV capsid assembly has been demonstrated in earlier works (Fernández-Arias A et al. 1998. Expression of ORF A1 of infectious bursal disease virus results in the formation of virus-like particles. Journal of General Virology 79:1047-1054). Expression in eukaryotic cells of the gene encoding for the IBDV polyprotein gives rise to the formation of VLPs that are completely indistinguishable, both morphologically and biochemically, from IBDV virions. It has also been observed that capsid assembly requires only the synthesis and correct processing of the viral polyprotein and is independent of the presence of the viral genome or of other proteins encoded by the viral genome, such as VP5 and VP1 proteins.

Until now, results obtained from the expression of IBDV genes in different recombinant systems has allowed concluding that: i) the assembly process is independent of the presence of genetic material of the virus, ii) only those polypeptides encoded by the polyprotein gene are required for assembly, and iii) assembly requires a coordinated interaction between polypeptides VP2 and VP3.

However, it is unknown if pVP2/VP3 interaction is established between VP2 and VP3 domains of the precursor polyprotein even when it has not been modified, or if, on the contrary, this interaction occurs after processing the precursor. Furthermore, current information does not exclude the possibility that VP4 could play a relevant role in capsid morphogenesis. In fact, IBDV VLPs formed by assembly of IBDV VP2, VP3 and VP4 proteins (U.S. Pat. Nos. 6,528,063; 5,788,970 and JP 5194597) have been disclosed.

The work developed by the inventors of this work has allowed establishing systems for obtaining IBDV VLPs by using different eukaryotic expression vectors. These vectors have been used for expressing the IBDV polyprotein in the absence or presence of viral polymerase RNA VP1. The biochemical characterization of purified VLPs shows that they contain pVP2, VP2 and VP3 proteins when only the viral polyprotein is expressed, and pVP2, VP2, VP3 and VP1 proteins when the polyprotein and the viral polymerase RNA are expressed simultaneously (Fernández-Arias A et al. 1998. Expression of ORF A1 of infectious bursal disease virus results in the formation of virus-like particles. Journal of General Virology 79:1047-1054; Martínez-Torrecuadrada J L et al. 2000. Different architectures in the assembly of infectious bursal disease virus capsid proteins expressed in insect cells. Virology 278:322-331; Maraver A et al. 2003. The oligomerization domain of VP3, the scaffolding protein of infectious bursal disease virus, plays a critical role for capsid formation. Journal of Virology 77:6438-49; Lombardo E et al. 1999. VP1, the putative RNA-dependent RNA polymerase of infectious bursal disease virus, forms complexes with the capsid protein VP3, leading to efficient encapsidation into virus-like particles. Journal of Virology 73:6973-6983).

Incidentally, patent document WO 02/088339 discloses IBDV viral-like particles formed by the assembly of chimeric proteins comprising the IBDV polyprotein bound to a polypeptide at its terminal carboxyl end.

CVLPs based solely on the IBDV pVP2 protein, or on fragments thereof, fused to a polypeptide of interest, or their potential use as vaccines or as carriers for products of interest, have not been described before.

SUMMARY OF THE INVENTION

The invention is faced with the problem of providing new tools to vectorize or incorporate in carriers, products of interest such as molecules with biological activity, for example drugs, polypeptides, proteins, nucleic acids, etc.

The solution provided by this invention is based on the inventors having observed that it is possible to obtain chimeric empty viral-like particles derived from IBDV as a result of expression of the IBDV pVP2 protein, or a fragment of said protein that is able to assemble itself and form said viral-like particles, which are genetically modified to include a nucleotide sequence encoding for a heterologous polypeptide comprising a polypeptide of interest, generically called IBDV CVLP-pVP2s* in this description. In fact, the inventors have observed that the full-length IBDV pVP2 protein, or a fragment of said protein of up to 501, typically 441-466, contiguous amino acid residues starting after amino acid one of the IBDV pVP2 protein, can be fused with a heterologous polypeptide and the fusion (chimeric) proteins thus obtained can be assembled together and form CVLPs, specifically said CVLP-pVP2s*, which have properties similar to those of the native viral capsids in terms of specificity and interactions with cells, and which can further be manipulated to be directed towards other target cells.

Said IBDV CVLP-pVP2s* are formed by the assembly of fusion proteins comprising a region A consisting of an IBDV pVP2 protein or by a fragment of said IBDV pVP2 protein comprising at least one sequence homologous to the sequence of the 1-n fragment of the IBDV pVP2 protein, where "n" is an integer comprised between 441 and 501, bound to a region B consisting of a heterologous polypeptide comprising a polypeptide of interest, where said region B is bound to the amino- or carboxyl-terminal end of said IBDV pVP2* protein. These CVLP-pVP2s* can be used for healthcare purposes, for example therapeutic, prophylactic or preventive, or diagnostic purposes, etc., for example in the preparation of vaccines, gene therapy vectors, etc.

Studies conducted by the inventors have surprisingly shown that it is possible to obtain CVLPs formed by fusion protein assembly comprising (i) IBDV pVP2 protein fragments (e.g., pVP2 fragments with 441 to 501, preferably from 441 to 466, contiguous amino acid residues starting after amino acid 1 of the IBDV pVP2 protein), and (ii) a heterologous amino acid sequence, and that said heterologous amino acid sequences are not an obstacle for forming said CVLPs. The inventors have also observed that said CVLPs can be used to effectively immunize birds against infection induced by IBDV or to effectively protect animals from infection induced by other causal agents (depending on the heterologous amino acid sequence present in said CVLPs and on the antigen/immunogen contained in said sequence).

In a particular embodiment, the inventors have obtained CVLPs formed by fusion protein assembly comprising IBDV pVP2 protein fragments (e.g., pVP2 fragments with 441 to 466 contiguous amino acid residues starting after amino acid 1 of the IBDV pVP2 protein) and a heterologous amino acid sequence, such as a histidine tag (Example 1). In another particular embodiment, the inventors have also observed CVLP formation by means of expression of IBDV pVP2 protein fragments, particularly the fragment identified in this description as protein pVP2-456, fused to the chimeric peptide of the foot-and-mouth disease virus (FMDV) called BT, comprising FMDV B and T cell epitopes (Example 3) (Zhang, Q. et al., 2002, Acta Virologica 46(1):1-9).

Producing CVLPs based on a single protein (pVP2*) has many advantages, both at the level of handling the expression vectors used and at the level of production yield, in comparison to the production of other CVLPs formed by the assembly of two proteins (e.g., the IBDV pVP2 protein and a fusion protein based on the IBDV VP3 protein).

Therefore, one aspect of the present invention is related to a fusion protein comprising a region A consisting of an IBDV pVP2 protein or a fragment of said IBDV pVP2 protein comprising at least one sequence homologous to that of fragment 1-n of the IBDV pVP2 protein, where "n" is an integer comprised between 441 and 501, bound to a region B consisting of a heterologous polypeptide comprising a polypeptide of interest. The process for obtaining said fusion protein constitutes an additional aspect of this invention.

In another aspect, the present invention is related to a chimeric empty viral-like particle, generically called IBDV CVLP-pVP2* (singular) or CVLP-pVP2s* (plural) in this description, characterized in that it is formed by the assembly of said fusion protein hereinbefore defined.

An additional aspect of this invention is related to a process for producing said IBDV CVLP-pVP2s* provided by this invention, based on the gene expression of said fusion protein hereinbefore defined.

Nucleic acids, expression cassettes, recombinant vectors and host cells developed for carrying out said process for producing said fusion proteins or said IBDV CVLP-pVP2s*, as well as their use for producing said IBDV CVLP-pVP2s* fusion proteins constitute additional aspects of the present invention.

Said IBDV CVLP-pVP2s* have the ability to vectorize or incorporate in carriers, products of interest such as molecules with biological activity, for example drugs, polypeptides, proteins, antibodies, nucleic acids, etc.

Therefore, in another additional aspect the present invention is related to the use of said IBDV CVLP-pVP2s* in preparing pharmaceutical compositions such as vaccines, gene therapy vectors and active substance delivery systems. Said vaccines, gene therapy vectors and active substance delivery systems constitute additional aspects of the present invention.

BRIEF DESCRIPTION OF THE FIGURES

FIG. 2A shows the circular dichroism (CD) spectrum of the peptide FGFKDIIRAIRRI (SEQ ID NO:1) in PES buffer, in the absence (broken line) or in the presence of 30% trifluoroethanol (TFE) (continuous line). The minimum at 208 and 220 nm and increased elliptical shape at 195 nm can be observed in the figure. In FIG. 2B, the secondary structure of the 241-250 residues of LmTIM is shown. See the amphipathic nature of the alpha helix.

Figure 3A:
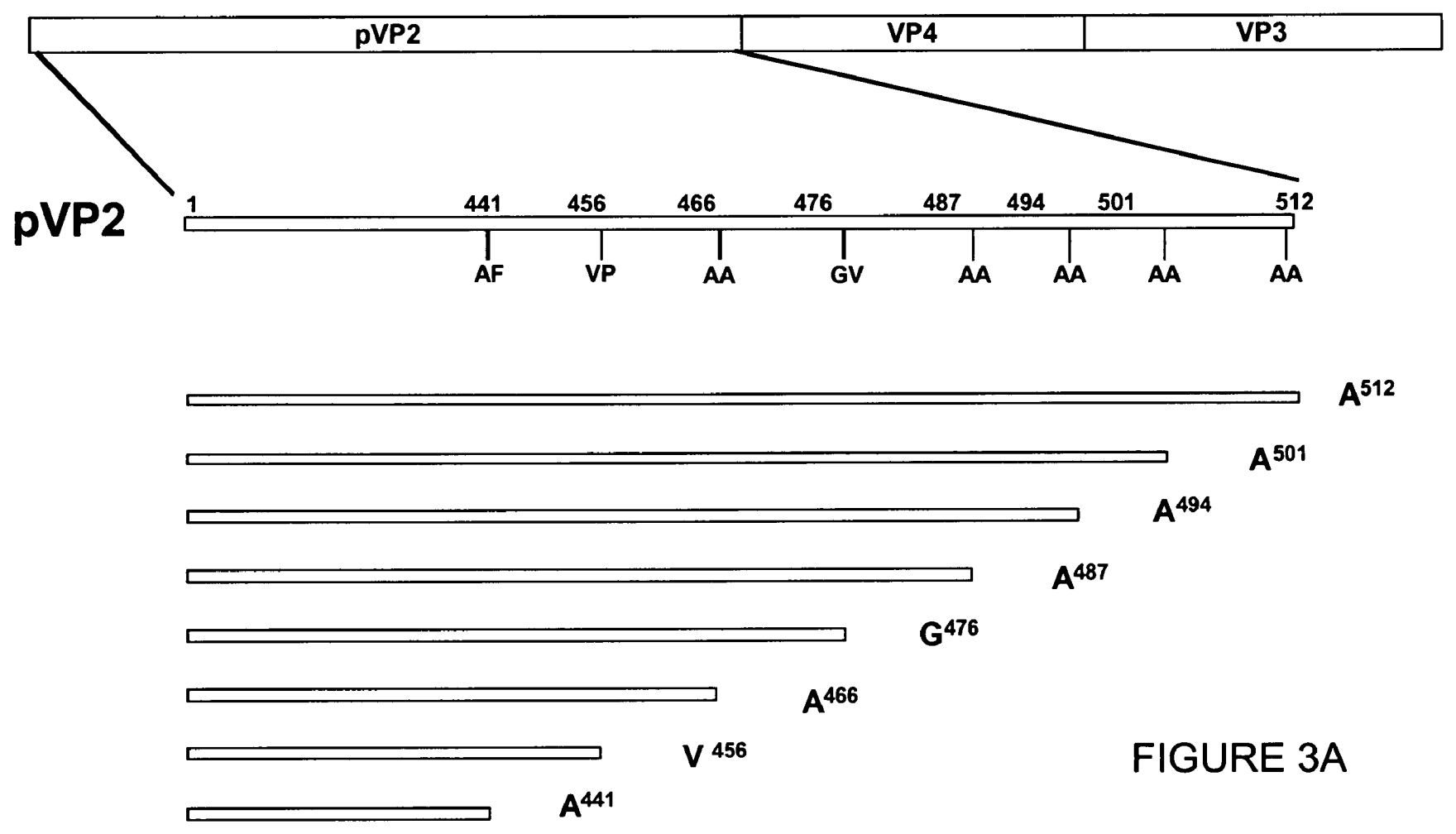
Figure 3:
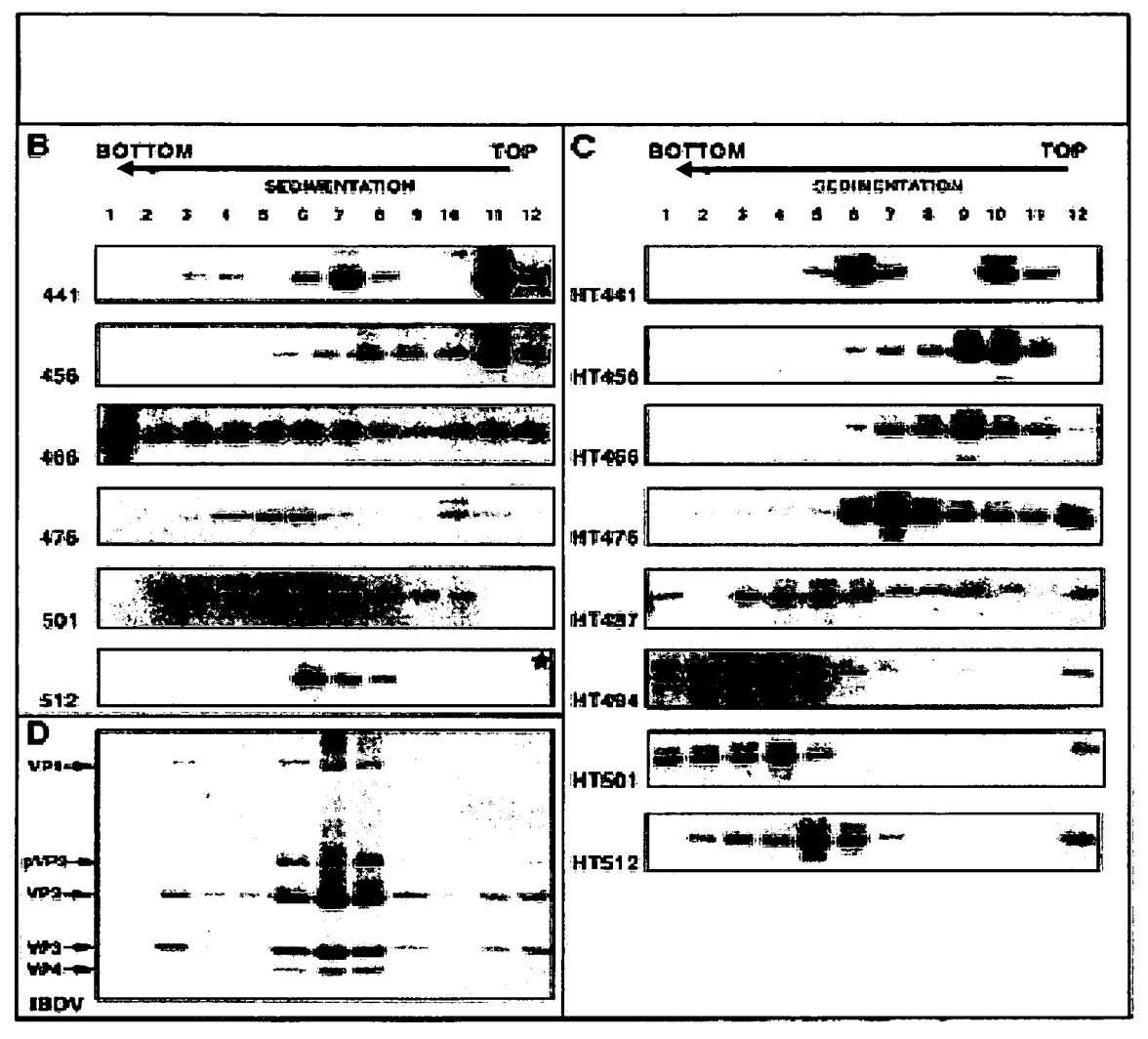

FIG. 3 shows an analysis of pVP2 proteins and of the HT-pVP2 mutant in SDS-PAGE gels stained with Coomassie blue. FIG. 3A shows a diagram of the pVP2 C-terminal region, and the positions and sequences that have been selected for deletions in the mutants are indicated. The His-tag mutant versions were also generated. Both the mutants with tag (FIG. 3C) and without tag (FIG. 3B) were expressed at high levels and centrifuged in two steps; 12 fractions were taken and concentrated 20 fold, then 1-10 μl of each fraction (0.1 μl per HT-pVP2 mutant) were loaded. They were analyzed by SDS-PAGE and developed by Coomassie staining. The asterisk indicates that the gel was analyzed by Western blot using an anti-VP2 antibody (VP2-512). The VP2-487 and VP2-494 mutants did not form sufficiently stable structures to resist the purification conditions, since they did not give a precipitate from the first sucrose gradient (result not shown). In FIG. 3D, the typical profile of IBDV proteins of cells infected with IBDV is shown. The sedimentation direction was from right to left, and fraction 12 represents the top part of each gradient.

FIGS. 4A and 4B show that VP2-441 and VP2-456 mutants form particles with capsids with symmetry T=1, despite the fact that some residue associated in unstable larger structures formed by 12 dodecahedral particles (arrows in FIG. 4A). FIGS. 4C, 4D and 4E show photographs of different VP2-466 assemblies: tubular structures with a hexagonal arrangement deduced from their Fourier transforms (insert) in the lower fractions are shown in en FIG. 4C, FIG. 4D shows particles with capsids T=1, broken slender tubes and disassociated material as predominant structures, and particles with capsids T=13 in the medium fractions were also obtained, and FIG. 4E shows particles with T=1 in the top fractions.

FIG. 5A shows the HT-VP2-441 assemblies: capsid structures with T=1 and larger dodecahedral assemblies (indicated with arrows). FIG. 5B shows HT-VP2-466 assemblies: particles with capsids with T=13 and T=7 in the intermediate fractions. FIG. 5C shows the assemblies of HT-VP2-466 particles with capsids T=13 and T=7 in the intermediate fractions. FIGS. 5D, 5E and 5F show HT-VP2-476 assemblies: type I tubular structures in the lower fractions (FIG. 5D), particles with capsids T=13 and T=7 and pieces with tubular assembly in the intermediate fractions (FIG. 5E), and irregular assemblies in the upper fractions (FIG. 5F). The bar corresponds to a length of 100 nm.

FIG. 6A shows a cryoelectron micrograph of IBDV capsids. The bar length is 50 nm. FIG. 6B shows a representation of the outer (left) and inner (right) surface of the IBDV capsid seen along a two-dimensional axis of icosahedral symmetry. The surface map has been represented by assuming the presence of 780 molecules of VP2-441 and a value of 0.73 cm³/g as a partial specific protein volume. In order to clearly see the envelope pores, only the front hemisphere of the map is shown. The five types of trimeric capsomers are indicated with letters a to e. The bar length is 200 Å.

FIG. 7A shows an electron cryomicroscopy photograph of the HT-VP2-466 assemblies (fraction 7). The bar length is 50 nm. Circles enclose three clearly distinguishable icosahedral assemblies with a symmetry T=13, T=7 and probably T=1. The bar length is 50 nm. FIG. 7B shows the three-dimensional structure of HT-VP2-466 capsids with T=13 (left and center) and T=7 (right). These density maps were profiled in order to encompass a volume of 780 (T=13) or 420 (T=7) HT-VP2-466 molecules. The HT-VP2-466 trimer types are indicated. The bar length is 200 Å.

FIG. 8A shows the density profiles of IBDV (continuous line) and HT-VP2-466 (dotted line) 3DR capsids, both analyzed at a resolution of 15 Å. The protein envelopes (r=253-350 Å) are virtually overlapping except for small differences (arrows). FIG. 8B shows a photograph of SDS-PAGE gel with Coomassie blue staining of proteins of the IBVD and HT-VP2-466 capsids used for the electron cryomicroscopy. pVP2/VP2 and VP3 were quantified from equal gels. FIGS. 8C and 8D show cross-sections of the capsids taken from IBDV and HT-VP2-4663DR, respectively. Protein and RNA are dark. FIG. 8E represents a map by calculating the difference between HT-VP2-466 and the IBDV capsid. The resulting map is represented on the outer surface of the IBDV capsid seen along a two-dimensional icosahedral axis. FIG. 8F represents a difference map calculated from the difference of IBDV with respect to the HT-VP2-466 capsid. Upon subtracting these differences, the resulting map, shown as 132 major lobes, is shown on the inner surface of the HT-VP2-466 capsid seen along a two-dimensional icosahedral axis. Each one of these density isles, using 0.73 cm³/g as a partial protein volume, corresponds to about 26 kDa. On the other hand, the mass of 5-6 copies of the segments of 442-466 (2.6 kDa) and His-Tag (3.4 kDa) range from 31 to 37 kDa each. The bar length is 200 Å.

FIG. 10A shows a diagram illustrating the assemblies adopted by VP2 with different C-terminal end extensions, depending on the C-terminal sequence extension, alone (VP2) or with His-tag (HT-VP2). The α-helix of the peptide 443-GFKDIIRAIR-453 (SEQ ID NO:2) is shown. It must be noted that as the length of the C-terminal sequence bound to VP2 (or its His-tag version) increases, there is a balance in the displacement among structures with capsids with T=1 and tubes, favoring the formation of hexagonal tubular structures. The complete sequence of the pVP2 C-terminal region and of the sites used in this invention is also shown. FIG. 10B shows a representation of the hereinbefore mentioned α-helix for the peptide GFKDIIRAIR (SEQ ID NO:2) on the left. The proposed complementary loading between the amphipathic α-helix and the last five amino acids of the VP3 C-terminal region (or the alignment of the similar VP3 His-Tag (H-tag) region) used in the present invention is shown on the right side of the figure. The VP3 and H-tag sequences are shown in opposite directions, from the C-terminal to the N-terminal region.

FIG. 11 shows the result of a Western blot analysis of different fractions (F6-F11) containing IBDV chimeric capsids formed by the assembly of the IBDV pVP2-456 protein and the chimeric BT peptide containing the Foot-and-Mouth Disease Virus, or FMDV, B and T epitopes expressed in yeasts. The upper blot shows the results obtained using a specific IBDV anti-VP2 antibody, whereas the lower blot shows the results obtained using a specific anti-FMDV antibody. Different immunoreactive bands (polypeptides) due to the existence of the aggregates producing the proteins when the capsids are formed can be observed in the upper blot; the same polypeptides are recognized by specific anti-FMDV antibodies (lower panel). The control (pESCURA/pVP2) shows an immunoreactive band against specific anti-VP2 antibodies with a smaller molecular weight that is not recognized by specific anti-FMDV antibodies.

DETAILED DESCRIPTION OF THE INVENTION

Figure 1:
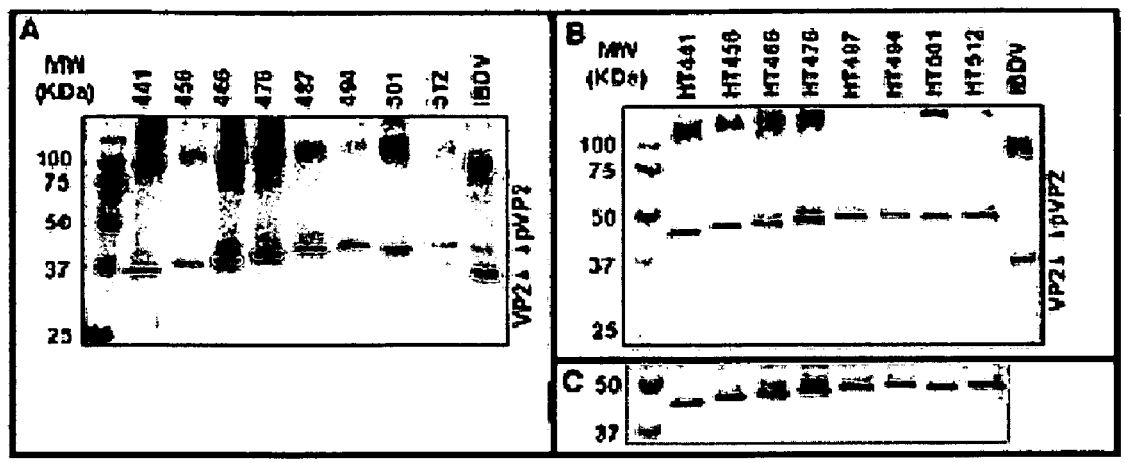
FIG. 1 shows the expression of deletion mutants of the C-terminal end of pVP2 with and without a His-tag on the N-terminal end. The collection of pVP2/VP2 expression mutants without (FIG. 1A) and with (FIG. 1B, 9C) His-tag was analyzed by SDS-PAGE and Western-blot by means of the use of an anti-VP2 (FIG. 1A, 1B) and anti-His (FIG. 1C) polyclonal antibody. The same volume of cell extract was loaded for each mutant in order to thus compare the relative levels of expression of pVP2/VP2 mutants. IBDV capsids were used as a positive control, and the positions corresponding to pVP2 and VP2 are indicated. Molecular weight markers are indicated on the left in kDa. For the sake of simplification, pVP2/VP2 mutants are referred to according to the position of the last amino acid. In order to assure that the VP3 protein is not present ant to thus discard possible contaminations, the Western-blot was controlled using anti-VP3 antibodies (not shown).
Figure 2:
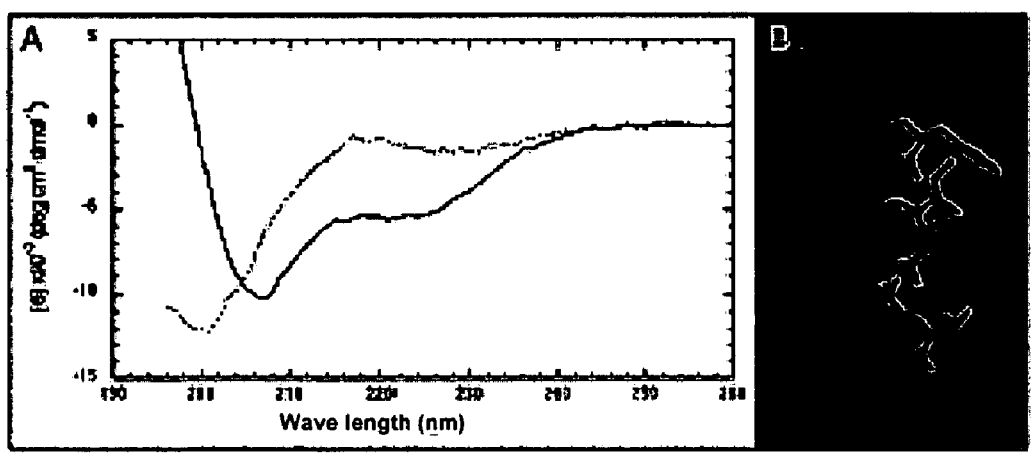
FIG. 2 shows an analysis of the pVP2 C-terminal end α-helix.

In a first aspect, the invention is related to a fusion protein, hereinafter fusion protein of the invention, comprising a region A consisting of the IBDV pVP2 protein or by a 1-n fragment of said IBDV pVP2 protein, where "n" is an integer comprised between 441 and 501, bound to a region B consisting of a heterologous polypeptide comprising a polypeptide of interest. Region B can be located in the N- or C-terminal position with respect to region A.

As it is used in the present invention, the term "IBDV" refers to the infectious bursal disease virus and includes different strains of IBDV belonging to any of the known serotypes (1 or 2) [by way of illustration, see the review by van den Berg T P et al. 2000. Rev Sci Tech. 19:509-43].

The term "IBDV pVP2 protein" generally refers to a protein the amino acid sequence of which consists of the amino acid sequence of the IBDV pVP2 protein and includes any of the different pVP2 proteins representative of any of the mentioned strains of IBDV (NCBI protein databank), according to the definition given by Sánchez and Rodríguez (1999) (Sánchez A B & Rodríguez J F. Proteolytic processing in infectious bursal disease virus: identification of the polyprotein cleavage sites by site-directed mutagenesis. Virology. 1999 Sep. 15; 262(1):190-199), as well as to proteins substantially homologous to said IBDV pVP2 proteins, i.e. proteins that present good alignment with the sequence of a certain IBDV pVP2 protein, for example proteins the amino acid sequences of which have a degree of identity with respect to said IBDV pVP2 proteins of at least 60%, preferably of at least 80%, more preferably of at least 90% and, even more preferably of at least 95%. Sequences homologous to a sequence of the IBDV pVP2 protein can easily be identified by a person skilled in the art with the aid of a computer program suitable for comparing sequences, for example the BLAST program (Altschul et al. 1997. Nucleic Acids Res. 25:3389). In a particular embodiment the IBDV pVP2 protein is the IBDV pVP2 protein Soroa strain, the full length amino acid sequence of which is deposited at the NCBI with accession number AAD30136 on May 13, 1999 (SEQ ID NO: 16).

The term "1-n fragment of the/said IBDV pVP2 protein, where "n" is an integer comprised between 441 and 501", generally refers to a peptide or protein the amino acid sequence of which consists of the contiguous amino acid sequence comprised between residue 1 and residue "n" of the IBDV pVP2 protein, where "n" is an integer comprised between 441 and 501. Therefore, said 1-n fragment of the IBDV pVP2 protein present, as the case may be, in the CVLP-pVP2s* provided by this invention, has an amino acid sequence consisting of, or comprising, between 441 and 501 residues of contiguous amino acids, starting from the residue of amino acid number 1, of any pVP2 protein representative of any IBDV strain, for example of the IBDV pVP2 protein Soroa strain [NCBI, access number AAD30136].

The particular 1-n fragments of the IBDV pVP2 protein are referred to following the format "pVP2-n", where "n" is as previously defined. In a particular embodiment, said 1-n fragment of the IBDV pVP2 protein is a protein selected from the group formed by:

(i) the pVP2-441 protein, the amino acid sequence of which consists of the sequence of contiguous amino acids comprised between residue 1 and residue 441 of the IBDV pVP2 protein;

(ii) the pVP2-452 protein, the amino acid sequence of which consists of the sequence of contiguous amino acids comprised between residue 1 and residue 452 of the IBDV pVP2 protein;

(iii) the pVP2-456 protein, the amino acid sequence of which consists of the sequence of contiguous amino acids comprised between residue 1 and residue 456 of the IBDV pVP2 protein;

(iv) the pVP2-466 protein, the amino acid sequence of which consists of the sequence of contiguous amino acids comprised between residue 1 and residue 466 of the IBDV pVP2 protein;

(v) the pVP2-476 protein, the amino acid sequence of which consists of the sequence of contiguous amino acids comprised between residue 1 and residue 476 of the IBDV pVP2 protein;

(vi) the pVP2-487 protein, the amino acid sequence of which consists of the sequence of contiguous amino acids comprised between residue 1 and residue 487 of the IBDV pVP2 protein;

(vii) the pVP2-494 protein, the amino acid sequence of which consists of the sequence of contiguous amino acids comprised between residue 1 and residue 494 of the IBDV pVP2 protein; and (viii) the pVP2-501 protein, the amino acid sequence of which consists of the sequence of contiguous amino acids comprised between residue 1 and residue 501 of the IBDV pVP2 protein.

The fusion protein of the invention comprises a region A consisting of the IBDV pVP2 protein or of a 1-n fragment of said IBDV pVP2 protein, where "n" is an integer comprised between 441 and 501, bound to a region B consisting of a heterologous polypeptide comprising a polypeptide of interest. In a particular embodiment, said region B is bound to the amino-terminal region of said IBDV pVP2 protein, whereas in another particular embodiment, said region B is bound to the carboxyl-terminal region of said IBDV pVP2 protein.

In a particular embodiment, said region A consists of the IBDV pVP2 protein. In this case, the IBDV pVP2 protein forming region A of the fusion protein of the invention can be any pVP2 protein representative of any IBDV strain, for example the full length IBDV pVP2 Soroa strain [NCBI, access number AAD30136].

In another particular embodiment, said region A consists of a 1-n fragment of said IBDV pVP2 protein. In this case, said 1-n fragment of the IBDV pVP2 protein forming region A of the fusion protein of the invention can be any 1-n fragment of a pVP2 protein representative of any IBDV strain, for example, of the Soroa strain. In a particular embodiment, said 1-n fragment of the IBDV pVP2 protein forming said region A is a protein chosen from the group formed by the pVP2-441 protein, the pVP2-452 protein, the pVP2-456 protein, the pVP2-466 protein, the pVP2-476 protein, the pVP2-487 protein, the pVP2-494 protein, and the pVP2-501 protein, preferably chosen from the pVP2-441 protein, the pVP2-452 protein, the pVP2-456 protein and the pVP2-466 protein.

Region B present in the fusion protein of the invention consists of a heterologous polypeptide comprising a polypeptide of interest. As it is used in the present invention, the term "heterologous polypeptide" refers to a polypeptide not belonging to the native IBDV capsid.

The size of the polypeptide of interest may vary within a broad range, from a few amino acids up to hundreds of amino acids. Said polypeptide of interest can be virtually any polypeptide, regardless of its origin (eukaryotic, prokaryotic, viral, etc.), susceptible of being expressed recombinantly, for example an antigen, such as a viral, bacterial, or microbial antigen, etc., against which it is desirable to induce an immune response in an animal (including human beings); an enzyme, such as an enzyme intended to supplement a function in which an organism is deficient; or a polypeptide comprising a nucleic acid-binding peptide domain able to specifically recognize a target DNA or RNA sequence that allows binding the fusion protein of the invention to a nucleic acid sequence comprising said target sequence, and its encapsidation in a viral-like particle comprising said fusion protein of the invention (IBDV CVLP-pVP2s*). In a particular embodiment, said polypeptide of interest is a polypeptide useful in vaccination, therapy or diagnosis, such as an epitope or antigenic determinant able to induce an immune response in animals and humans against diseases caused by viruses, bacteria, parasites or any other type of microorganisms, or against tumor diseases. In a specific embodiment, said polypeptide of interest is the chimeric peptide of the foot-and-mouth-disease virus (FMDV) called BT, which comprises FMDV B cell epitopes (B epitope) and T cell epitopes (T epitope) (Zhang, Q. et al., 2002, Acta Virologica 46(1):1-9). In a particular embodiment, the B epitope is located in the FMDV VP1 protein, for example between positions 133-159 of said Spanish serotype C isolate VP1 protein, or in equivalent positions of other isolates, whereas the T epitope is located in the FMDV VP4 protein, for example between positions 20-34 of said FMDV serotype Asia VP4 protein.

In a particular embodiment, said region B comprises a single polypeptide of interest. However, in another particular embodiment, said region B comprises two or more identical or different polypeptides of interest which may form tandems.

In a particular embodiment, the fusion protein of the invention comprises a region A bound to a single region B. In this case, said region B can be bound to the amino-terminal region of said IBDV pVP2 protein or of said 1-n fragment of the IBDV pVP2 protein; or alternatively, said region B may be bound to the carboxyl-terminal region of said IBDV pVP2 protein or of said 1-n fragment of the IBDV pVP2 protein.

As previously discussed, region B may contain one or more polypeptides of interest. In a particular embodiment, said region B contains a single polypeptide of interest, whereas in another particular embodiment, said region B comprises two or more different polypeptides of interest.

In another particular embodiment, the fusion protein of the invention comprises a region A bound to two regions B, one of them bound to the amino-terminal region of the IBDV pVP2 protein or of said 1-n fragment of the IBDV pVP2 protein present in region A and the other one to the carboxyl-terminal region of the IBDV pVP2 protein or of said 1-n fragment of the IBDV pVP2 protein present in region A. Said regions B can be identical or different and each one of them can contain one or more polypeptides of interest, which can be identical to or different from one another. In a specific embodiment, the fusion protein of the invention comprises a region A bound to a first region B containing a first polypeptide of interest (B1) and a second region B containing a second polypeptide of interest (B2). Said polypeptides of interest (B1) and (B2) can be identical or different. In a specific embodiment, said polypeptides of interest (B1) and (B2) are different from one another.

Region A of the fusion protein of the invention can be bound directly to said region B. Alternatively, said region A is not bound directly to said region B, but rather it is bound through a linker polypeptide between said regions A and B. Therefore, if desired, the fusion protein of the invention can further contain a linker polypeptide located between said regions A and B. Advantageously, said linker polypeptide is a peptide with structural flexibility, preferably a polypeptide that gives rise to a non-structured domain able to induce an immune response or not. By way of illustration, said flexible peptide can contain repetitions of amino acid residues, particularly of Gly and Ser residues, or any other suitable repetition of amino acid residues.

The fusion protein of the invention can be obtained by means of gene expression of the nucleic acid sequence encoding for said fusion protein in suitable host cells. Said suitable host cells are cells containing the nucleotide sequence encoding for the fusion protein of the invention, for example cells containing a nucleic acid sequence containing the nucleotide sequence encoding for the fusion protein of the invention or which have been transformed by said nucleic acid, or cells transformed, transfected or infected with a recombinant vector comprising a nucleic acid sequence encoding for the fusion protein of the invention. The nucleic acid sequences, expression cassettes, recombinant vectors and host cells that are suitable for obtaining the fusion protein of the invention shall be described below in detail in combination with the process for producing IBDV CVLP-pVP2s*.

The fusion protein of the invention expressed in a suitable host cell may assemble itself and form chimeric empty viral-like particles derived from IBDV generically called IBDV CVLP-pVP2* (singular) or IBDV CVLP-pVP2s* (plural) in this description.

Therefore, in another aspect, the invention is related to said IBDV CVLP-pVP2s*. Said IBDV CVLP-pVP2s* are formed by assembly of the fusion protein of the invention, they have symmetry T=1 and are characterized in that they consist only of assembling fusion proteins of the invention comprising a region A consisting of the IBDV pVP2 protein or of a 1-n fragment of said IBDV pVP2 protein, where "n" is an integer comprised between 441 and 501, bound to a region B consisting of a heterologous polypeptide comprising a polypeptide of interest.

The IBDV CVLP-pVP2s* of the invention can be obtained by means of expressing the fusion protein of the invention in suitable host cells under conditions allowing the formation of said viral-like particles of IBDV.

Therefore, in another aspect, the invention provides a nucleic acid the nucleotide sequence of which comprises the nucleotide sequence encoding for the fusion protein of the invention.

In a particular embodiment, the nucleic acid sequence of the invention comprises (i) a nucleotide sequence comprising the open reading frame or encoding region corresponding to the IBDV pVP2 protein or to a 1-n fragment of said IBDV pVP2 protein, where "n" is an integer comprised between 441 and 501, and (ii) a nucleotide sequence comprising the open reading frame or encoding region of one or more heterologous polypeptides comprising one or more polypeptides of interest.

In another particular embodiment, the sequence of the nucleic acid provided by this invention comprises (i) a nucleotide sequence comprising the open reading frame or encoding region corresponding to the IBDV pVP2 protein or to a 1-n fragment of said IBDV pVP2 protein, where "n" is an integer comprised between 441 and 501, (ii) a first nucleotide sequence comprising the open reading frame or encoding region of one or more heterologous polypeptides comprising one or more polypeptides of interest, and (ii') a second nucleotide sequence comprising the open reading frame or encoding region of one or more heterologous polypeptides comprising one or more polypeptides of interest, where said second nucleotide sequence may be identical to or different from said first nucleotide sequence. In this case, one of said first or second nucleotide sequences is operatively bound to the 5' end of the nucleotide sequence comprising the open reading frame or encoding region corresponding to said IBDV pVP2 protein or to said 1-n fragment of said IBDV pVP2 protein, and the other one is operatively bound to the 3' end of the nucleotide sequence comprising the open reading frame or encoding region corresponding to said IBDV pVP2 protein or to said 1-n fragment of said IBDV pVP2 protein.

As it is used in this description, the term "open reading frame corresponding to the IBDV pVP2 protein" or "open reading frame corresponding to a 1-n fragment of the IBDV pVP2 protein" includes, in addition to the nucleotide sequences of said open reading frames, other open reading frames similar to the same ones encoding the pVP2 proteins and 1-n fragments, where "n" is an integer comprised between 441 and 501, of said IBDV pVP2 protein.

Likewise, the term "open reading frame of one or more heterologous polypeptides comprising one or more polypeptides of interest", includes any encoding nucleotide sequence of said heterologous polypeptide(s) comprising one or more polypeptides of interest. The term "analogous" as it is herein used aims to include any nucleotide sequence that may be isolated or constructed on the basis of the encoding nucleotide sequence of the IBDV pVP2 protein or of the 1-n fragment, where "n" is an integer comprised between 441 and 501, of said IBDV pVP2 protein, for example by means of introducing conservative or non-conservative nucleotide substitutions, including the insertion of one or more nucleotides, the addition of one or more nucleotides on any end of the molecule or the deletion of one or more nucleotides on any end or within the sequence. Generally, a nucleotide sequence similar to another nucleotide sequence is substantially homologous to said nucleotide sequence.

In the sense that it is used in this description, the expression "substantially homologous" means that the nucleotide sequences in question have a degree of identity, at the nucleotide level, of at least 60%, preferably of at least 80%, more preferably of at least 90% and even more preferably of at least 95%.

In another aspect, the invention provides an expression cassette comprising a nucleic acid sequence provided by this invention, i.e. a nucleic acid the nucleotide sequence of which comprises the nucleotide sequence encoding for the fusion protein of the invention operatively bound to transcription, and optionally translation, control elements.

In a particular embodiment, the expression cassette provided by this invention comprises, operatively bound to transcription, and optionally translation, control elements, a nucleotide sequence comprising (i) a nucleotide sequence comprising the open reading frame or encoding region corresponding to the IBDV pVP2 protein or to a 1-n fragment of said IBDV pVP2 protein, where "n" is an integer comprised between 441 and 501, and (ii) a nucleotide sequence comprising the open reading frame or encoding region of one or more heterologous polypeptides comprising one or more polypeptides of interest.

In another particular embodiment, the expression cassette provided by this invention comprises, operatively bound to transcription, and optionally translation, control elements, a nucleotide sequence comprising (i) a nucleotide sequence comprising the open reading frame or encoding region corresponding to the IBDV pVP2 protein or to a 1-n fragment of said IBDV pVP2 protein, where "n" is an integer comprised between 441 and 501, (ii) a first nucleotide sequence comprising the open reading frame or encoding region of one or more heterologous polypeptides comprising one or more polypeptides of interest, and (ii') a second nucleotide sequence comprising the open reading frame or encoding region of one or more heterologous polypeptides comprising one or more polypeptides of interest, where said second nucleotide sequence can be identical to or different from said first nucleotide sequence. In this case, one of said first or second nucleotide sequences is operatively bound to the 5' end of the nucleotide sequence comprising the open reading frame or encoding region corresponding to said IBDV pVP2 protein or to said 1-n fragment of said IBDV pVP2 protein, and the other one is operatively bound to the 3' end of the nucleotide sequence comprising the open reading frame or encoding region corresponding to said IBDV pVP2 protein or to said 1-n fragment of said IBDV pVP2 protein.

The transcription, and optionally translation, control elements present in the expression cassette provided by this invention include promoters which direct transcription of the nucleotide sequences (IBDV pVP2 or fragment thereof and heterologous polypeptide) to which it is operatively linked, and other sequences necessary or suitable for transcription and its suitable regulation in time and place, for example beginning and termination signals, cleavage sites, polyadenylation signals, replication origin, transcriptional enhancers, transcriptional silencers, etc. Generally, said elements, as well as the vectors used to construct the expression cassettes and the recombinant vectors according to the invention, are chosen according to the host cells intended to be used.

In another aspect, the invention provides a recombinant vector comprising a nucleic acid sequence provided by this invention or an expression cassette provided by this invention. Virtually any vector can be used in generating the recombinant vector provided by this invention. By way of illustration, said suitable expression systems or vectors can be chosen according to the conditions and needs of each specific case, from said plasmids, bacmids, yeast artificial chromosomes (YACs), bacteria artificial chromosomes (BACs), bacteriophage P1-based artificial chromosomes (PACs), cosmids, or viruses, which can further have a heterologous replication origin, for example a bacterial or yeast origin, so that it can be amplified into bacteria or yeasts, as well as a marker that can be used to select the transfected cells that are different from the gene or genes of interest. These recombinant vectors can be obtained by persons skilled in the art by means of using conventional genetic engineering techniques (Sambrook et al. 1989. Molecular Cloning: A Laboratory Manual. 2nd Ed. Cold Spring Harbor Laboratory Press, Cold Spring Harbor, N.Y.), and they are part of the present invention.

In a particular embodiment, said recombinant vector is a plasmid, such as a plasmid suitable for transforming yeasts, or a virus, such as a recombinant baculovirus (rBV) expressing the fusion protein of the invention during its replication cycle and which, after their assembly, form IBDV CVLP-pVP2s*. In a particular embodiment CVLPs, specifically IBDV CVLP-pVP2s* containing the FMDV chimeric BT peptide in the C-terminal position with respect to the pVP2-456 protein, have been obtained in yeasts. The expression plasmid pESCURA/pVP2-456-BT, which was used to transform *Saccharomyces cerevisiae* cultures (Example 3), was generated for this purpose. In another particular embodiment CVLPs have been obtained by means of using an rBV-based expression system (Example 1).

In another aspect, the invention provides a host cell containing a nucleic acid sequence provided by this invention, i.e. the nucleotide sequence encoding for the fusion protein of the invention. In a particular embodiment, said host cell is a cell transformed by a nucleic acid sequence provided by this invention containing the nucleotide sequence encoding for the fusion protein of the invention. In another particular embodiment, said host cell is a cell that is transformed, transfected or infected with a recombinant vector provided by this invention comprising a nucleic acid sequence of the invention containing a nucleotide sequence encoding for the fusion protein of the invention.

Virtually any host cell susceptible to being transformed by a nucleic acid sequence provided by this invention, or any host cell susceptible to being transformed, transfected or infected by a recombinant vector provided by this invention can be used, for example mammal cells, bird cells, insect cells, yeasts, etc.; nevertheless, in a particular embodiment, said host cell is selected from yeasts and insect cells. Yeasts are suitable due to simplicity and production costs. Insect cells are suitable when the expression system comprises an rBV. The use of rBV is advantageous for biosafety issues relating to the baculovirus host range of baculoviruses, which are unable to replicate in cell types that are not insect cells.

In a particular embodiment, the invention provides a host cell, such as a yeast, for example a yeast of the *Saccharomyces* genus, such as *S. cerevisae, S. pombe*, etc., or of the *Pichia* genus, such as *P. pastoris*, etc., transformed with a recombinant vector provided by this invention, such as a plasmid comprising a nucleic acid sequence of the invention or an expression cassette provided by this invention comprising the nucleotide sequence encoding for the fusion protein of the invention.

In another particular embodiment, the invention provides a host cell, such as an insect cell, infected with a recombinant vector provided by this invention, such as an rBV comprising a nucleic acid sequence of the invention or an expression cassette provided by this invention comprising the nucleotide sequence encoding for the fusion protein of the invention.

In another aspect, the invention provides a process for producing IBDV CVLP-pVP2s* comprising culturing a host cell provided by this invention containing the nucleotide sequence encoding for the fusion protein of the invention and expressing said protein and, if desired, recovering said IBDV CVLP-pVP2s*. In a particular embodiment, said process is carried out by means of using a host cell provided by this invention consisting of a cell transformed by a nucleic acid sequence of the invention comprising the nucleotide sequence encoding for the fusion protein of the invention. In another particular embodiment, said process is carried out by using a host cell provided by this invention consisting of a cell that is transformed, transfected or infected with a recombinant vector provided by this invention comprising a nucleic acid sequence of the invention containing a nucleotide sequence encoding for the fusion protein of the invention.

After expressing the fusion proteins of the invention in said cells, the expressed proteins are assembled and form IBDV CVLP-pVP2s*, which can be isolated or removed from the medium and purified if so desired. The isolation and purification of said IBDV CVLP-pVP2s* can be done by conventional methods, for example by means of sucrose gradients fractioning.

In a particular embodiment, gene expression of the fusion protein of the invention is done by means of using an rBV that allows expressing the fusion protein of the invention from the nucleic acid sequence provided by this invention in insect cells. Therefore, in a particular embodiment, the invention provides a process for producing IBDV CVLP-pVP2s* comprising (i) culturing insect cells infected with an rBV comprising the nucleotide sequence encoding for the fusion protein of the invention, under conditions that allow expressing the recombinant proteins and their assembly to form IBDV CVLP-pVP2s*, and (ii) if so desired, isolating, and optionally purifying said IBDV CVLP-pVP2s*. Said process therefore comprises first obtaining a recombinant vector consisting of an rBV comprising a nucleic acid sequence of the invention or an expression cassette provided by this invention comprising the nucleotide sequence encoding for the fusion protein of the invention, followed by infecting insect cells with said rBV, expressing recombinant proteins, and if so desired, isolating the IBDV CVLP-pVP2s* formed by assembling the fusion protein of the invention, and optionally subsequently purifying said IBDV CVLP-pVP2s*.

The construction of a recombinant baculovirus that allows expressing the fusion protein of the invention can be carried out by a person skilled in the art based on that herein described and in the state of the art regarding this technology (Sambrook et al. 1989. Molecular Cloning: A Laboratory Manual. 2nd Ed. Cold Spring Harbor Laboratory Press, Cold Spring Harbor, N.Y.; Leusch M S et al. 1995. A novel host-vector system for direct selection of recombinant baculoviruses (bacmids) in *Escherichia coli*. Gene 160:91-4; Luckow V A et al. 1993. Efficient generation of infectious recombinant baculoviruses by site-specific transposon-mediated insertion of foreign genes into a baculovirus genome propagated in *Escherichia coli*. J Virol 67:4566-79).

In another particular embodiment, gene expression of the fusion proteins of the invention can be done by means of using a recombinant vector that allows expressing the fusion protein of the invention in yeast cells. Therefore, in a particular embodiment, the invention provides a process for producing IBDV CVLP-pVP2s* comprising (i) culturing yeasts transformed with a recombinant vector comprising the nucleotide sequence encoding for the fusion protein of the invention, under conditions that allow expressing the recombinant proteins and their assembly to form IBDV CVLP-pVP2s*, and (ii) if so desired, isolating and optionally purifying said IBDV CVLP-pVP2s*. Said process therefore comprises first obtaining a recombinant vector consisting of a plasmid comprising a nucleic acid sequence of the invention or an expression cassette provided by this invention comprising the nucleotide sequence encoding for the fusion protein of the invention, followed by transforming yeasts with said recombinant vector, expressing recombinant proteins, and if so desired isolating the IBDV CVLP-pVP2s* formed by assembling the fusion protein of the invention, and optionally subsequently purifying said IBDV CVLP-pVP2s*. In a specific embodiment, the suitable expression system for transforming yeasts is based on a pESC yeast expression system (Stratagene). Obtaining yeasts transformed with a suitable recombinant vector that allows expressing the fusion protein of the invention, can be done by a person skilled in the art based on that herein described and in the state of the art regarding this technology (pESC epitope tagging vectors instruction manual (Stratagene); Sambrook et al. 1989. Molecular Cloning: A Laboratory Manual. 2nd Ed. Cold Spring Harbor Laboratory Press, Cold Spring Harbor, N.Y.). Generally, the IBDV CVLP-pVP2s* obtained in yeasts are capsids T=1; by way of illustration, when IBDV CVLP-pVP2s*, in which region A consists of the pVP2-441 protein, the pVP2-456 protein or the pVP2-466 protein, were produced in yeasts, the IBDV CVLP-pVP2s* thus obtained were only capsids T=1.

In another aspect, the invention is related to the use of the recombinant vector provided by this invention for producing and obtaining the fusion protein of the invention and/or the IBDV CVLP-pVP2s* of the invention.

The IBDV CVLP-pVP2s* can be used as vectors or as carriers for products of interest, such as molecules with biological activity, for example drugs, polypeptides, proteins, antibodies, hormones, enzymes with therapeutic potential for treating diseases, nucleic acids, etc., so they can be used for therapeutic, diagnostic or research purposes. In a particular embodiment, said molecules of biological interest include polypeptides of interest, such as immune response antigens or inducers in animals or humans in whom it is delivered, so they can be used in preparing vaccines against human and animal diseases caused by viruses, bacteria, parasites or any other type of microorganisms, or against tumor diseases, or they include nucleic acid sequences useful in gene therapy, intended for being introduced inside suitable cells, so they can be used in preparing gene therapy vectors, or they include compounds of sanitary interest (antibodies, hormones, enzymes with therapeutic potential for treating diseases, etc.) for their administration to a human or animal body, so they can be used as active substance delivery systems.

Therefore, in another aspect the invention is related to the use of IBDV CVLP-pVP2s* in preparing a pharmaceutical composition, for example vaccines, gene therapy vectors, active substance delivery systems, etc. In a particular embodiment, said pharmaceutical composition is a vaccine intended for conferring protection against human or animal diseases caused by viruses, bacteria, parasites or any other type of microorganisms, or against tumor diseases. In another particular embodiment, said pharmaceutical composition is a gene therapy vector. In another particular embodiment, said pharmaceutical composition is an active substance delivery system; illustrative and non-limiting examples of said active substances include drugs, antibodies, hormones, enzymes potentially involved in treating diseases, etc.

In another aspect, the invention provides a vaccine comprising a therapeutically effective amount of IBDV CVLP-pVP2s*, optionally with one or more pharmaceutically acceptable adjuvants and/or carriers. Said vaccine is useful in protecting animals and humans against diseases caused by microorganisms (viruses, bacteria, parasites, etc.), or against tumor diseases. In a particular embodiment, said vaccine is particularly useful in protecting animals and humans simultaneously against infection caused by two or more disease-inducing infectious agents. By way of illustration, the vaccine provided by this invention can be used to protect birds, for example, chickens, turkeys, geese, ganders, pheasants, quails and ostriches, etc., against IBDV and against one or more infectious agents responsible for avian diseases (avian pathogens).

In the sense used in this description, the expression "therapeutically effective amount" refers to the calculated amount of IBDV CVLP-pVP2s* for producing the desired effect, and it will generally be determined, among other causes, by the typical characteristics of IBDV CVLP-pVP2s* and the immunization effect to be obtained.

The pharmaceutically acceptable adjuvants and carriers that can be used in said vaccines are adjuvants and carriers known by those skilled in the art and conventionally used in preparing vaccines.

In a particular embodiment, said vaccine is prepared as a solution or aqueous suspension in a pharmaceutically acceptable diluent, such as saline solution, phosphate buffered saline (PBS) solution, or any other pharmaceutically acceptable diluent.

The vaccine provided by this invention can be administered by any suitable administration method resulting in an immune response protecting against the heterologous sequence or epitope used, for which reason said vaccine shall be formulated in the pharmaceutical form that is suitable for the chosen administration method. In a particular embodiment, administration of the vaccine provided by this invention is carried out parenterally, for example intraperitoneally, subcutaneously, etc.

In another aspect, the invention is related to an active substance delivery system comprising at least one IBDV CVLP-pVP2* and one active substance. Illustrative, non-limiting examples of active substances include drugs, antibodies, hormones, enzymes with therapeutic potential for treating diseases, etc.

The following examples illustrate the invention and should not be considered in any sense that limits said invention.

EXAMPLE 1

Obtaining IBDV CVLP-pVP2s* in Insect Cells and Analyzing Structural Polymorphism I. Materials and Methods Preparation of the Virus The IBDV Soroa strain, a serotype I IBDV strain, was purified by a standard protocol from quail muscle QM7 cells (Lombardo et al. 1999. VP1, the putative RNA-dependent RNA polymerase of infectious bursal disease virus, forms complexes with the capsid protein VP3, leading to efficient encapsidation into virus-like particles. *J Virol* 73, 6973-6983) and was stored in 25 mM PES buffer (piperazine-N-N'-bis(2-ethanesulfonic acid) [PIPES] pH=6.2, 150 mM NaCl and 20 mM $CaCl_2$).

Construction of the Recombinant Baculoviruses

The recombinant baculovirus (rBV) FB/VP2-456 has previously been described (Castón et al., 2001. C terminus of infectious bursal disease virus major capsid protein VP2 is involved in definition of the T number for capsid assembly. *J Virol* 75, 10815-10828).

The plasmid pVOTE.2/POLY (Oña et al., 2004. The C-terminal domain of the pVP2 precursor is essential for the interaction between VP2 and VP3, the capsid polypeptides of infectious bursal disease virus. *Virology* 322, 135-142.) has been used as a DNA mold for PCR synthesis of DNA fragments of those derived from pVP2 to generate the rBVs identified as FB/VP2-441, FB/VP2-476, FBNVP2-476, FB/VP2-487, FBNVP2-494, FB/VP2-501 and FBNVP2-512. PCR was carried out with Vent DNA polymerase (Biolabs) using the same primer for the 5' end (5'-pVP2) and a specific primer for the 3' end of each mutant (Table 1).

TABLE 1

Oligonucleotide Primer Sequences Used to Generate C-terminal End Mutant Deletions

| Primer | Sequence (5'→3') |
|---|---|
| 5'-VP2 | GCGCAGATCTATGACAAACCTGTCAGATCAAACCC SEQ ID NO:3 |
| NotI-441 | GCGCGCGGCCGGTTATGCTCCTGCAATCTTCAGG SEQ ID NO:4 |
| HindIII-456 | GCGCAAGCTTACACAGCTATCCTCCTTATGGC SEQ ID NO:5 |
| HindIII-466 | GCGCAAGCTTAGGCAGGTGGGAACAATGTGG SEQ ID NO:6 |
| HindIII-476 | GCGCAAGCTTAACCTTCCCCAATTGCATGGGC SEQ ID NO:7 |
| HindIII-487 | GCGCAAGCTTAGGCCTGGGCCTCATCGCCCAGC SEQ ID NO:8 |
| HindIII-494 | GCGCAAGCTTAGGCTCGAGCAGTTCCTGAAGC SEQ ID NO:9 |
| HindIII-501 | GCGCAAGCTTAAGCTCTTGCTTTTCCTGACGC SEQ ID NO:10 |
| HindIII-512 | GCGCAAGCTTAGGCGAGAGTCAGCTGCCTTATGC SEQ ID NO:11 |

Fragments of PCR digestion with BglII-HindIII were cloned into the multiple (polylinker) cloning sites BamHI-HindIII of protein expression plasmids FastBac and pHisFastBac-C (Invitrogen). The plasmid pHisFastBac-C was used to express the His-pVP2 variants. The extra tag sequence that was used is MSYYHHHHHHDYDIPTTENLYFQ-GAMGS. (SEQ ID NO:12) The resulting plasmid sequences were checked by means of the Sanger sequencing method (Sanger et al., 1977. DNA sequencing with chain-terminating inhibitors. *Proc Natl Acad Sci USA* 74, 5463-5467).

Selection of the bacmids derived from the *E. coli* DH10Bac strain and the preparation thereof for their transfection with lipofectamine was carried out according to protocols of the manufacturers (Invitrogen).

The constructs were expressed in H5 insect cells (Maraver et al., 2003. Identification and molecular characterization of the RNA polymerase-binding motif of infectious bursal disease virus inner capsid protein VP3. *J Virol* 77, 2459-2468) (FIG. 1).

Characterization and Purification of the pVP2 Deletion Mutant Structures

H5 cells (2-5×10$^8$ cells) were infected with the suitable rBV at an multiplicity of infection (m.o.i.) of 1-5 plaque forming units (PFU)/cell. The cells were collected at 48 hours post-infection (h.p.i.) and were lysed in PES lysis buffer containing 1% of IGEPAL CA-630 (Sigma) in ice. The particle material was purified through a 20% sucrose cushion and a 25-50% linear sucrose gradient. The particle material that contained the pVP2 deletion mutated protein was concentrated 20 fold by ultracentrifugation and was identified by means of SDS-PAGE and Western blotting. Fractions rich in VP2 were selected for structural studies and were used within the first 1-2 days after purification.

SDS-PAGE and Western Blotting

The cell extracts of the infected cells (10-15 μl) or the fractions of the sucrose concentration gradient (2-5 μl) were added to the Laemmli buffer until reaching a final concentration of 1×, was heated (100° C., 2 minutes). Electrophoresis was carried out in 11% polyacrylamide gels (38.96% (w/v) acrylamide and 1.04 (w/v) bis-acrylamide methylene). Western blotting was carried out with an anti-VP2 serum (Lombardo et al., 1999. VP1, the putative RNA-dependent RNA polymerase of infectious bursal disease virus, forms complexes with the capsid protein VP3, leading to efficient encapsidation into virus-like particles. *J Virol* 73, 6973-6983). Rabbit anti-VP3 serum was used as the negative control. The anti-His tag antibody was obtained from Sigma.

Conventional Electron Microscopy 2-5 μl samples of each fraction of the sucrose gradient were arranged and stained negatively with 2% (w/v) aqueous uranyl acetate. The micrographs were recorded with a JEOL 1200 EXII electron microscopy operating at 100 kV at a nominal magnification of ×40,000.

Electron Microscopy

The samples (5 μl drops), or fractions containing the virions or HT-VP2-466 capsids, were arranged on mesh coated with coal, washed two times with water drops, dried by blotting, and were submerged in a liquid ethane bath following established processes, essentially as disclosed by Castón et al. (Castón et al. 2001. C terminus of infectious bursal disease virus major capsid protein VP2 is involved in definition of the T number for capsid assembly. *J Virol* 75, 10815-10828). The micrographs were recorded under minimum exposure conditions such that the captured samples received exposures of 6-10 e$^-$/nm$^2$, at nominal magnifications of ×50,000 in a Tecnai G2 electron microscopy operating at 200 kV and equipped with a field device. The bacteriophage T4 was vitrified and the axial spacing of 40.5 Å of its tail sheath was used as an internal magnification standard.

Circular Dichroism (CD) Microscopy

Figure 4:
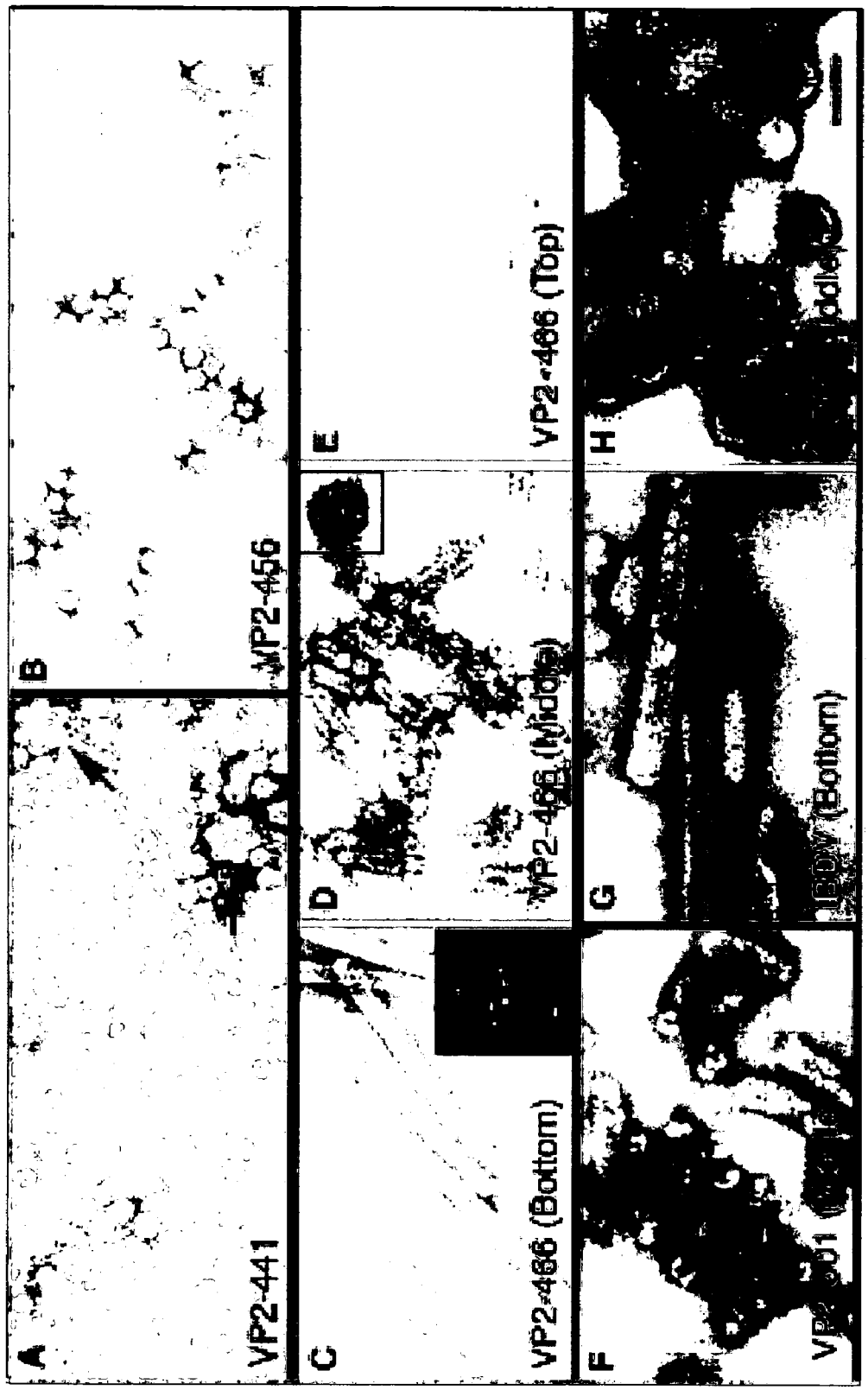
FIG. 4 represent electron microscopy photographs of the assembly of pVP2 of the C-terminal region deletion mutants.
Figure 5:
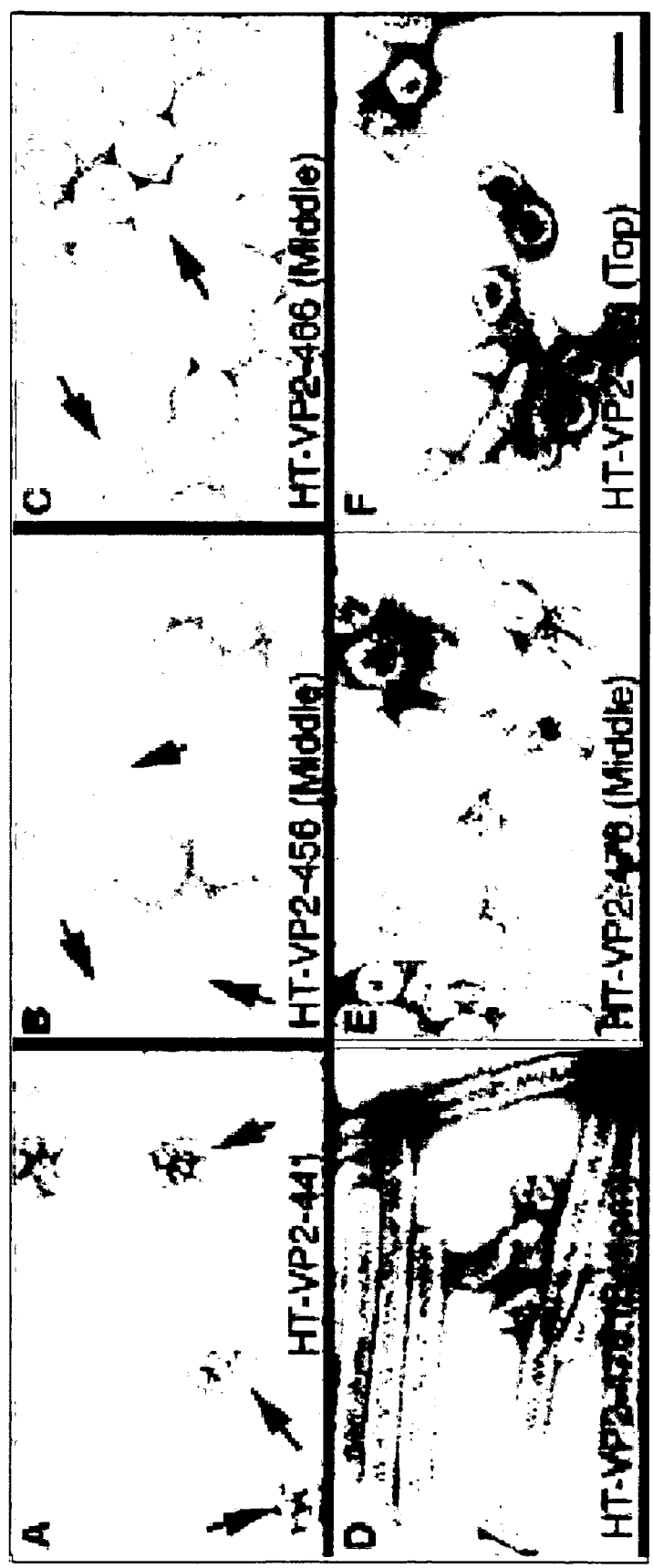
FIG. 5 consists of photographs obtained by electron microscopy of the assemblies corresponding to the mutant proteins His-pVP2 with deletions in the C-terminal region. The concentration fractions were diluted (⅕₀) for optimal observation of the obtained assemblies.
Figure 6:
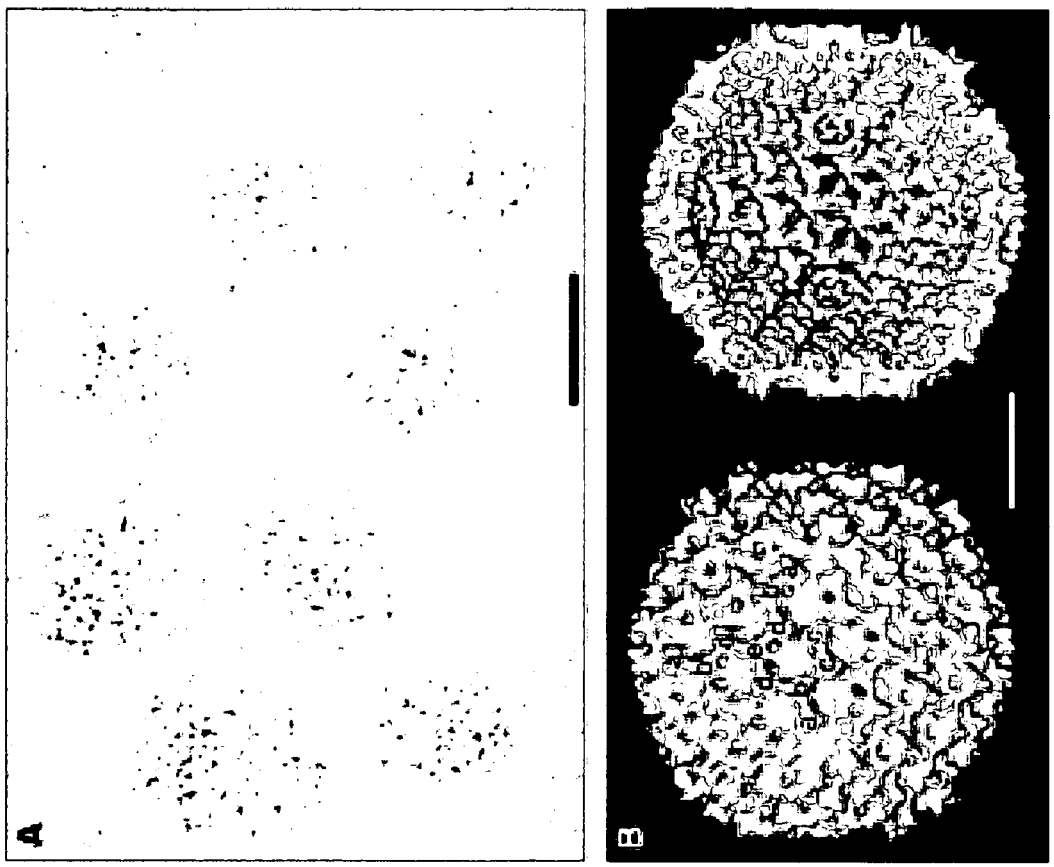
FIG. 6 shows the three-dimensional structure of the IBDV capsid.
Figure 7:
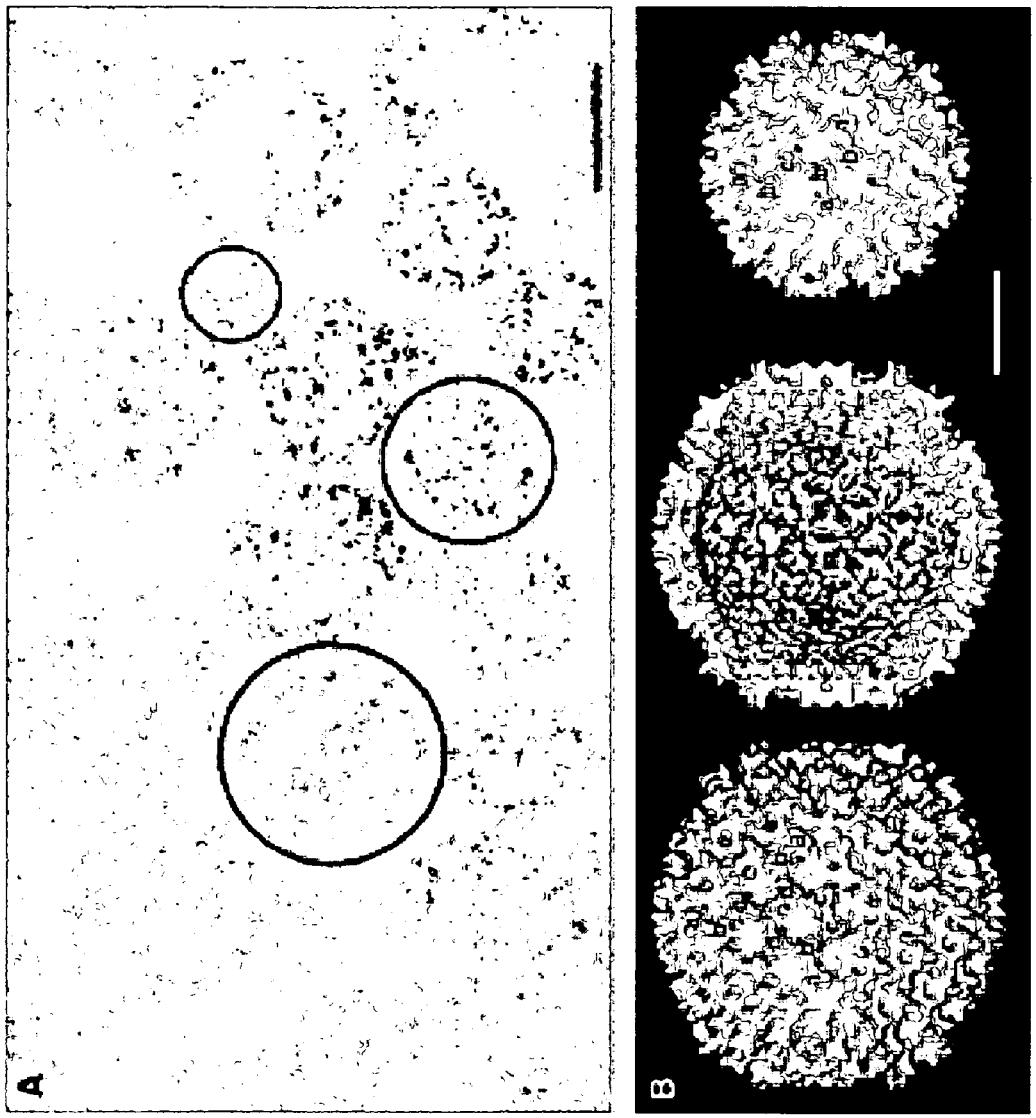
FIG. 7 shows the three-dimensional structure of HT-VP2-466 capsids.

The peptide FGFKDIIRAIRRI (SEQ ID NO:1) was chemically synthesized and its far UV CD spectrum was stored in a Jasco dichrograph using cells with size 0.1 to 1 mm at 25° C. Each spectrum is the accumulation of 3 scanners. The peptide concentrations used range from 10 to 200 μM. The CD spectrum was analyzed as previously described by Jiménez, 1999 (Jiménez et al., 1999. Helicity of alpha (404-451) and beta (394-445) tubulin C-terminal recombinant peptides. *Protein Sci* 8, 788-799) (FIG. 4A).

Image Analysis

General image processing operations were performed using a PIC software system (Trus et al. 1996. Digital image processing of electron micrographs: the PIC system-III. *J Struct Biol* 116, 61-67). The micrographs were assessed in terms of their resolution and astigmatism by Fourier analysis. The sub-focal value of the selected electron micrographs allowed reconstructing the structures at a resolution within the first zero of the electron microscopy contrast transfer function (CTF). The sub-focal values for the analyzed selected micrographs (81 for IBDV, 82 for the HT-VP2-466 capsids), measured with the Bsoft package (Heymann, 2001), ranged from 0.6 to 3.7 μM (CTF at spaces of 12-30 Å , respectively). The micrographs were acquired with a Zeiss PhotoScan TD scanner at 7 μm/pixel and binned to produce 21 μm pixels (4.2 Å in the sample). The protein particles were extracted and pre-processed using the automated process of Conway et al. (Conway et al., 1993. The effects of radiation damage on the structure of frozen hydrated capsids HSV-1. *J Struct Biol* 111, 222-233). The first estimates of the angular orientations of the particles were measured by "common line" processes in Fourier Transforms (PFT) (Baker and Cheng, 1996. A model-based approach for determining orientations of biological macromolecules imaged by cryoelectron microscopy. *J Struct Biol* 116, 120-130), using the IBDV 3DR as a starting model, at an approximate scale, at 28 Å resolution. A new density map was calculated and was used for all refinements of the subsequent phase orientation and origin, using a modified version of the PFT algorithm such that both amplitude and phase information can be used.

Only model-based processes were used to reconstruct the small VP2 capsid, and another small VP2 capsid extracted from the large VP2 capsid was used as a starting model. Its three-dimensional structure was calculated as an internal control without imposing icosahedral symmetry using a weighted back-projection method and distributing the orientations throughout the entire orientation space by randomly selecting equivalent views that were related to the original ones by symmetry. The resulting density map was similar to the one obtained with the method based on icosahedral symmetry but at a lower resolution (data not shown). The phases were corrected for the contrast transfer function (CTF) by means of simple transposition of the required CTF lobule phases. The reconstructs were calculated using the Fourier-Bessel techniques (Crowther, 1971. Procedures for three-dimensional reconstruction of spherical viruses by Fourier synthesis from electron micrographs. *Phil Trans R Soc Ser B* 261, 221-230). The final reconstructs combined 10,849 and 1,557 images for IBDV and HT-VP2-466 capsids, and the resolutions obtained by means of the envelope Fourier correlation criterion (0.5 threshold) of 12 and 15 Å, respectively. Another reconstruct for smaller HT-VP2-466 capsids was calculated from the same set of micrographs. The final reconstruct resolution, which contained 108 particles, was estimated at approximately 23 Å according to the estimate obtained by FSC analysis (Convay et al., 1993. The effects of radiation damage on the structure of frozen hydrated HSV-1 capsids. *J Struct Biol* 111, 222-233).

Spherically quantified radial density profiles were calculated for both maps of T=13 and were normalized and taken to scale to overlap both profiles. The maps were then obtained by the difference of both and changing the order of the two maps. Small density isles were filtered to translate the results of both maps (see FIGS. 8E and 8F), considering only the greater differences in radiuses corresponding to the protein envelope.

II. Results pVP2 Protein C-Terminal End Deletion Mutants Having a His-Tag on their N-Terminal End Given that processing of the pVP2 protein C-terminal end (512 amino acids) giving rise to the VP2 protein (441 amino acids) does not occur when expressed in recombinant baculoviruses, different pVP2 constructs have been expressed in said system which vary in C-terminal end length. Positions 456, 466, 476, 487, 494 and 501 (FIG. 3A) have been selected in order to uniformly cover said region. Western blot analysis of these pVP2/VP2 variants shows that all the pVP2 mutants with C-terminal deletions are correctly expressed, giving rise to a major band (FIG. 1). The same series of pVP2/VP2 mutants, fused at their N-terminal end to a His-tag (HT-VP2), have also been generated. The molecular weights of said pVP2/VP2 variants are shown in Table 2.

TABLE 2

| Molecular Weight (kDa) of the pVP2/VP2 Variants | | |
|---|---|---|
| Mutant-(last residue) | −6x Histidines | +6x Histidines |
| VP2-441 | 47.1 | 50.5 |
| VP2-456 | 48.9 | 52.2 |
| VP2-466 | 49.9 | 53.3 |
| VP2-476 | 50.8 | 54.2 |
| VP2-487 | 52.0 | 55.3 |
| VP2-494 | 52.6 | 56.0 |
| VP2-501 | 53.2 | 56.6 |
| VP2-512 | 54.4 | 57.8 |

The pVP2/VP2 variants were expressed at high levels and purified by means of a sucrose cushion followed by a sucrose gradient. The fractions obtained from the gradient were characterized by SDS-PAGE electrophoresis. The gels stained with Coomassie blue showed that the fractions containing the pVP2 variants had a very broad range of bands (FIGS. 3B, 3C). The fusion proteins obtained from cells infected with IBDV following the strategy described hereinbefore were purified for the purpose of comparing said results (FIG. 3D). While the pVP2 mutants not containing His-tag showed a heterogeneous organization (FIG. 3B), the pVP2/VP2 fusion proteins containing His-tag are organized such that their size increases as the C-terminal domain length increases (FIG. 3C).

Electron Microscopy Analysis of pVP2/VP2 Assemblies

The analyses of the different protein fractions obtained from the sucrose gradient, which were negatively stained by electron microscopy, showed a different morphology depending on the pVP2 C-terminal end length and on the presence or absence of His-tag.

VP2-441 (FIG. 4A) and VP2-456 (FIG. 4B) gave rise to donut shaped assembly structures of about 23 nm in diameter corresponding to that of dodecahedral capsids with symmetry T=1. Depending on the VP2-466 assembly type being formed, the variant is thus situated through the sucrose gradient. The lower fractions contained thin tubes with a diameter of about 25 nm (FIG. 4C), regularly arranged with a helical morphology (FIG. 4C, box). The fractions of the medium showed shorter thin tubes with capsids of symmetry similar to T=1 surrounded by material interrupting them, indicating that this symmetry is probably very unstable (FIG. 4D). Symmetries similar to T=13 were also occasionally observed (FIG. 4D, box). The predominant structures in the upper part of the gradient were small isometric particles (FIG. 4E). VP2-476 behaves in a manner similar to VP2-466. Most of the VP2-501s migrated to fractions in the bottom half of the gradient and assembled into partially arranged tubes of about 35 nm in diameter (FIG. 4F). In the upper half part of the gradient, VP2-501 assembles into an isometric twisted tubule structure with an irregular size. VP2-512 was finally observed as curved short tubules and as irregular particles.

In the cells infected by IBDV, most of the purified structures were located in the middle of the gradient and correspond with an icosahedral particle of diameter 65-70 nm (FIG. 4H). Nevertheless, tubular-shaped structures with hexagonal organization called type I tubes were observed close to the bottom of the gradient (FIG. 4G).

All these results together show that VP2-466 contains sufficient information for forming hexamer (thin tube) and pentamer (capsid T=1) type capsids, and capsids with assembly T=13 were sporadically observed.

Electron Microscopy Analysis of (His-) pVP2/VP2 Assemblies

Assemblies of the HT-pVP2NVP2 fusion proteins were similarly analyzed. The occurrence of particles 23 nm in diameter was observed in the HT-VP2-441 enrichment fractions (FIG. 5A). The mutant HT-VP2-456 produced the assembly of structures with a morphology similar to real infectious capsids T=13 (compare FIGS. 5B and 4H), which migrated to the middle of the gradient. Most of the HT-VP2-456s, capsids T=1, were located in the upper part of the gradient. The tendency to form correct capsids was improved with the HT-VP2-466 protein (FIG. 5C). Particles with capsids similar to T=13 were shown with a greater abundance, and as they were being obtained with a high efficiency, they were selected for high resolution structural studies. Capsids with a mean size of about 53 nm could be easily distinguished from capsids T=13 (FIG. 5C, arrows).

The HT-VP2-476 (FIGS. 5D-F) and HT-VP2-487 fusion proteins maintained the ability to be assembled as capsids with a structure similar to the viruses, although with a lower efficiency. The predominant structures were hexagonal tubes of variable lengths (FIG. 5D). Finally, the HT-VP2-494, HT-VP2-501 and HT-VP2-512 proteins formed only tubular structures with an apparently hexagonal arrangement.

The His-tag N-terminal end of the different pVP2/VP2 proteins did not affect the assembly of the subunits in regular particles. In the absence of the VP3 protein, the other major component of the capsids, HT-VP2-456, allowed the correct assembly of structures with symmetry similar to capsids T=13.

Circular Dichroism Analysis of Amino Acids 443-452 of the pVP2 C-Terminal Domain The secondary structure of the peptide GFKDIIRAIR (SEQ ID NO:2), which corresponds to amino acids 443-452 of the pVP2 protein C-terminal end, was predicted by means of the Agadir computer program (Munoz and Serrano, 1994. Elucidating the folding problem of helical peptides using empirical parameters. *Nat Struct Biol* 1, 399-409). Said program detected a pronounced helical tendency in the peptide, which gave rise to an amphipathic α-helix (FIG. 10B, left). In order to contrast this prediction, a synthetic peptide, amino acids 442-454, was synthesized and the average of the secondary structure was analyzed by circular dichroism. In an aqueous buffer, the peptide showed insignificant helical structure, such that it adopted a random winding formation. When trifluoroethanol (TFE), which is a helix-inducing solvent, is added, it resulted in the formation of a clearly helical component (FIG. 2). A search was conducted in the PDB (Protein Data Base) with WHATIF (on the world wide web) to see if peptides with similar known structures could be found, and said peptide was found in amino acids 241-250 of the *Leishmania mexicana* triosephosphate isomerase (Lm TIM) (Williams et al., 1999. Structural and mutagenesis studies of *leishmania* triosephosphate isomerase: a point mutation can convert a mesophilic enzyme into a superstable enzyme without losing catalytic power. *Protein Eng* 12, 243-250). When said sequence, EFRDIIDATR, (SEQ ID NO:13), is compared to the ten pVP2 amino acids, it is observed that the amphipathic nature is almost identical: there is a conservative change (R for K), a substitution of D with R, which changes the polarity by maintaining one side of the chain loaded, and a change of T for I.

Structure of the IBDV Capsid

A cryomicrograph of the IBDV particles shows clear peripheral indented areas (FIG. 6A). The final density map of the capsid T=13 was calculated with a resolution of 12 Å. The molecular architecture of the capsid is essentially like that disclosed by Böttcher et al. (Böttcher et al., 1997. Three-dimensional structure of infectious bursal disease virus determined by electron cryomicroscopy. *J Virol* 71, 325-330) in which the main characteristic is the presence of 260 V-P2 trimers projecting from a continuous envelope and arranged in five types of different formations (FIG. 6B a-e). On the inner side there are 200 inner Y-shaped trimeric projections. The improvement in resolution allowed identifying a number of structural details in a more accurate and precise manner, particularly in the five axes of the inner capsid. In this manner the 60 absent inner trimers, five per pentamer, are replaced by two annular edges. While the most outer edge is formed by ten closely connected globular densities, the inner edge is formed by five globules, as had been predicted (FIG. 9). Another relevant aspect is related to the porous appearance of the capsular envelope. These pores (616 in all) have a diameter of about 15 Å, and are located exactly under density connections, called connecting arms, between adjacent trimers on the outer side.

Structure of the His-VP2-466 Capsid

The electron microscopy analysis of the fractions rich in viral-like particles shows that the VP2-466 capsids are formed by a complex mixture of different capsids but which have a similar assembly (FIG. 7A). These capsids have an approximate size ranging from 65 nm (similar to the IBDV capsids T=13) to 53 nm, also with a variation of smaller isometric assemblies. All these structures showed the same peripheral indented areas. The HT-VP2-466 capsid 3DR was measured with a resolution of 15 Å (FIG. 7B, left and center). The outer sides of the IBDV and HT-VP2-466 capsids are almost overlapping, while the inner sides show apparent differences. The greater structural difference is related to the fivefold and sixfold axes of symmetry, where an extra density is observed that connects the structure of the Y-shaped trimer in the HT-VP2-466 capsid, and not in the IBDV capsid.

The density map of intermediate size HT-VP2-466 capsids showed symmetry T=7 (FIG. 7B, right), which was based on equivalence with the trimeric capsomers like those of T=13, except for the requirement of only three different types of triangular capsomers (called a', b' and c'). Capsids T=13 and T=7 share the same essential trimeric block of HT-VP2-466 in the icosahedral lattice.

Structural and Biochemical Comparison of IBDV and HT-VP2-466 Capsids

Structural similarities were found both in the radial density profiles (FIG. 8A) and in the central cross-sections (FIGS. 8C and 8D) of the IBDV and HT-VP2-466 capsids, which are virtually overlapping. Two minor differences were found in the protein coating (approximate radius 253 Å-350 Å) (FIG. 8A, arrows). An extra density peak was observed on the inner side of the IBDV capsid, mainly located at a radius of 325 Å-345 Å, and another one in the HT-VP2-466 capsid on its inner side (at a radius of 268 Å-285 Å). Difference maps were calculated by means of arithmetic subtraction of the density values of the protein sheath in both structures in order to more precisely locate said differences. By alternating the subtraction order in the two maps, the resulting maps showed only those structural differences which could be attributed to each structure (FIGS. 8E and 8F). The location of the structural differences on the outer side of the IBDV capsid shows that the regions with greater differences are in the connecting arms between adjacent VP2 trimers. The structural differences on the inner side are mainly in the fivefold and sixfold axes of symmetry, precisely where the inner densities of the HT-VP2-466 capsid are located.

Figure 8:
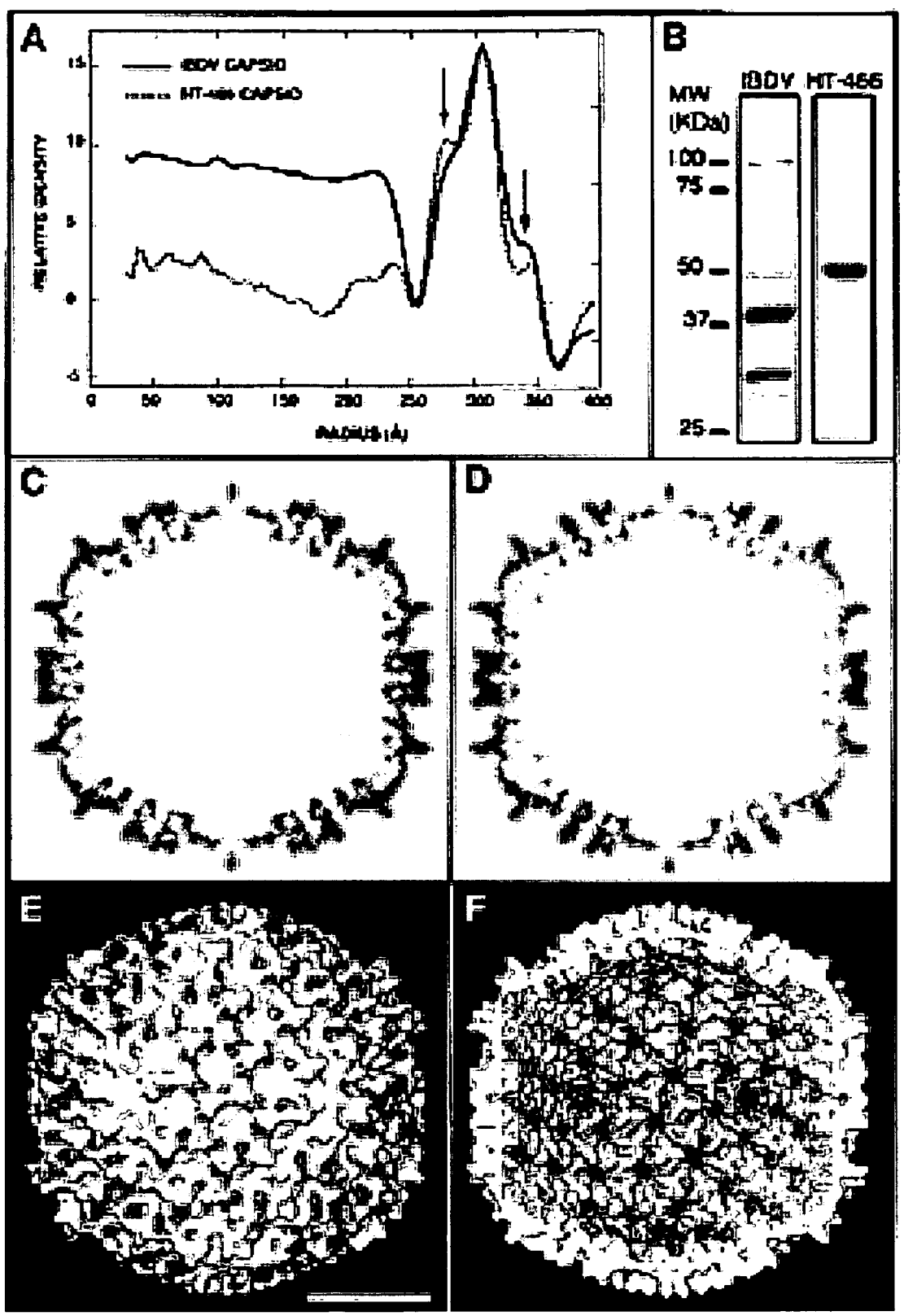
FIG. 8 shows a structural comparison of IBDV and HT-VP2-466 capsids.

Staining SDS-PAGE gels with Coomassie blue showed that the enriched fractions of viral particles contain pVP2/VP2 and VP3 as the main components (FIG. 8B), comprising almost 90% of the total protein. An equivalent analysis of the fractions used to obtain the electron cryomicroscopy data for the HT-VP2-466 capsids showed that said capsids consist of a single polypeptide of about 54 kDa. Since the minimum differences at the protein sheath level cannot be taken into account to check the differences with VP3, the obtained results mean that both capsids are constructed from a single protein, VP2, or its variant His-tag, for the IBDV and HT-VP2-466 capsids, respectively, and that VP3 is not incorporated as an integral component of the IBDV capsid.

Analysis of Quasi-Equivalence in a Capsid T=13

Figure 9:
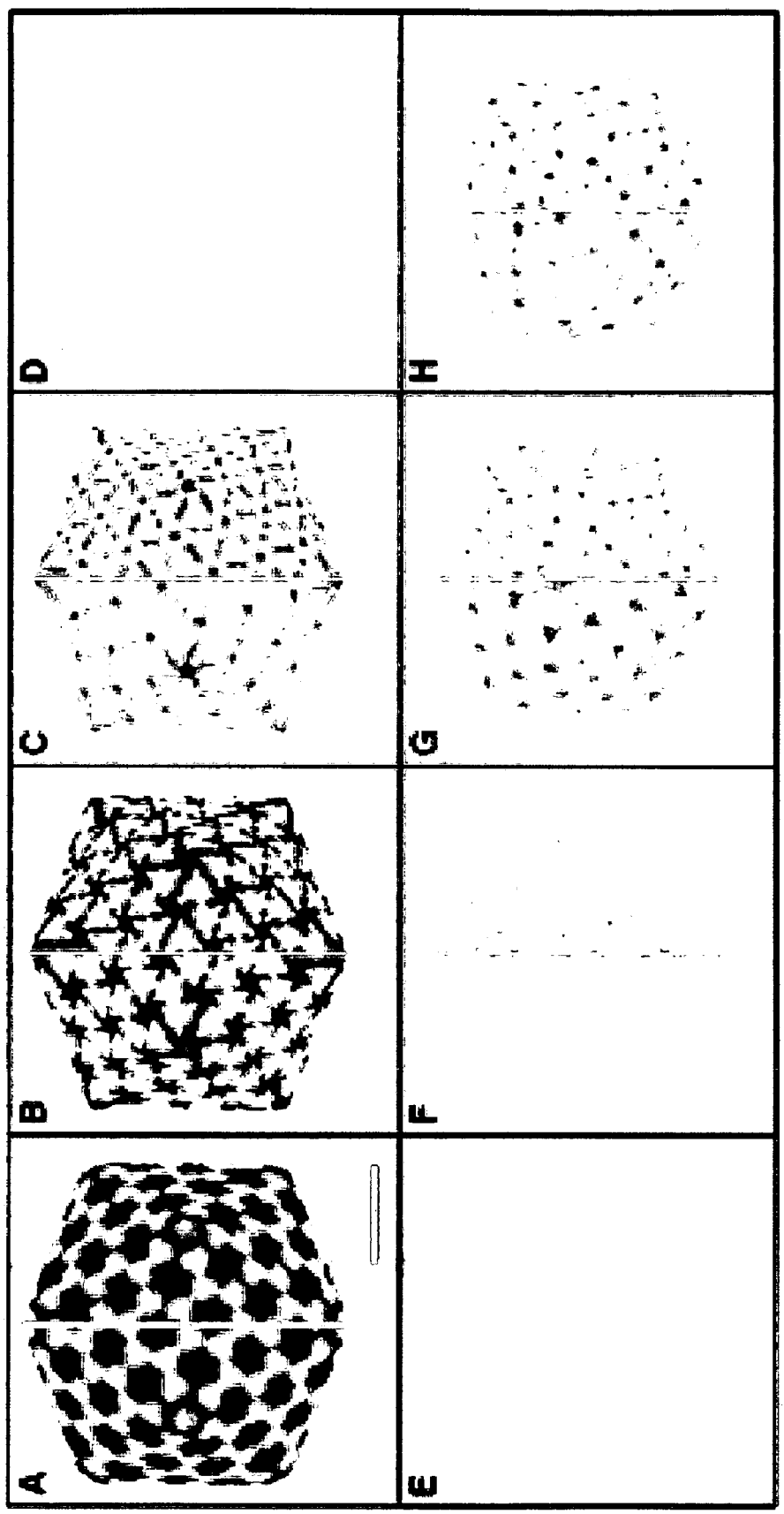
FIG. 9 shows the structural organization of the IBDV and HT-VP2-466 capsids. Icosahedral sections of IBDV (left half) and of HT-VP2.466 (right half) 3DR capsids are shown at a resolution of 15 Å, and seen under a two-dimensional axis. The perpendicular distances of the icosahedral sections that are shown from the center of capsids with T=13 are 328 Å (A), 319 Å (B), 311 Å (C), 302 Å (D), 294 Å (E), 286 Å (F), 277 Å (G) and 269 Å (H). The facets have been generated from the Facets program (provided by R. A. Crowther, MRC, Cambridge). The bar length is 200 Å.
Figure 10:
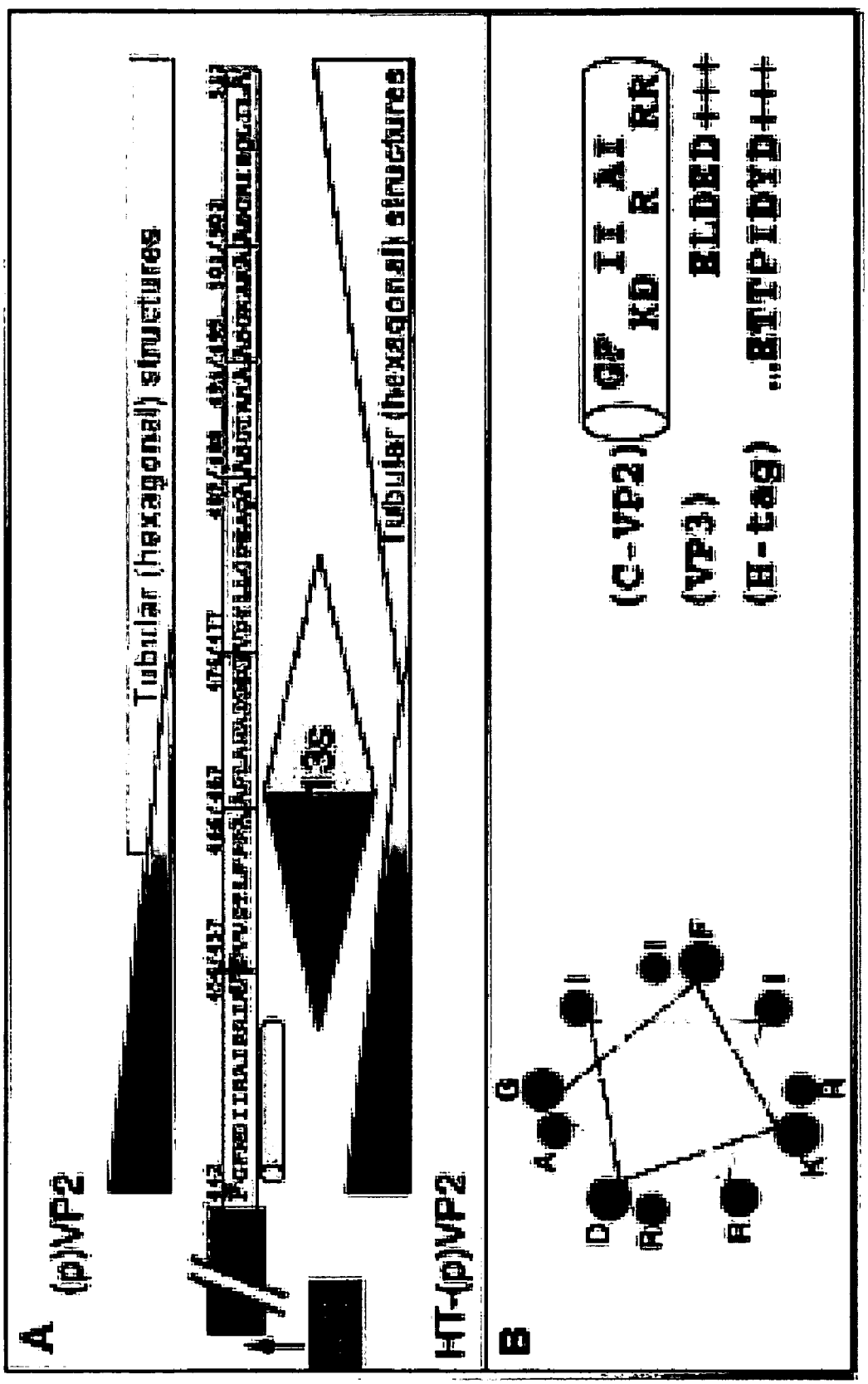
FIG. 10 shows the pVP2 and HT-pVP2 mutant protein assemblies.

A new scenario must be considered for the IBDV capsid, since this capsid must be considered a quasi-equivalent capsid. In order to confirm this hypothesis and suitably asses the equivalent characteristics of the IBDV and HT-VP2-466 capsids, alignment maps of icosahedral sections of said capsids were compared (FIG. 9). The most outer sections (de 328 a 311 Å) showed that the trimeric units were basically identical (FIGS. 9A, 9B and 9C). Furthermore, the continuous capsid is evident at (302 to 294 Å), and minimal differences are observed (FIGS. 9D and 9E). At a radius of 286 Å, the sections corresponding to the beginning of the inner layer of both capsids T=13 showed that the 260 inner trimeric units showed clear continuity with 260 other inner trimeric units, including those around the fivefold axis of symmetry (FIG. 9F). The pentameric trimers are more closely assembled than the hexameric trimers and appear fused at a radius of 277 Å, where there are visible extra densities in sixfold axes of symmetry of the HT-VP2-466 capsid (FIG. 9G). Extra densities in axes of symmetry of order 6 (FIG. 9H) are evident at a radius of 269 Å.

DISCUSSION

The conformation polymorphism of the most abundant protein in IBDV, the VP2 protein, has been analyzed in the present invention. VP2 is initially synthesized as a 512 amino acid precursor, pVP2, which is processed several times at its C-terminal end to give rise to the mature VP2 protein (441 amino acids). Most of the mutants expressed in the baculovirus system developed in this invention could therefore correspond to intermediates occurring naturally during the virus assembly process. The molecular mechanism responsible for controlling the polymorphisms is in a 71 amino acid sequence temporarily bound to the C-terminal end and which is removed when its function has been completed. In the absence of VP3, the presence of a His-tag at the N-terminal end of the VP2 protein is required for its correct assembly, indicating that this His-tag reproduces the function of the VP3 protein during assembly. Control of the assembly of the IBDV capsid T=13 complex therefore requires the independent interaction of two polypeptide elements which can be disconnected in the system of the present invention.

The results of the present invention indicate that the molecular controller of the VP2 protein change is located in the 443-GFKDIIRAIR-453 (SEQ ID NO:2) segment, which is arranged in α-helix shape. The HT-VP2-456 mutant of the invention represents the border between the forming a single conformation or multiple conformations in VP2. If the assembly units are shorter, as in the case of HT-VP2-441, only pentameric structures are produced (capsids T=1), whereas if amino acids 443-452 are included, both capsids T=13 and capsids T=1 are formed.

EXAMPLE 2

Characterization of IBDV CVLP-pVP2s* Immunogenicity

In order to evaluate the immunogenicity of the CVLPs-pVP2-456 obtained in Example 1, an immunization test was conducted in 1 day-old chickens. In summary, a group of 7 SPF (specific pathogen-free) animals were immunized intramuscularly with a single dose of 200 µl containing 10 µg of CVLPs-pVP2-456/animal diluted in PBS. A similar group was injected with PBS. Serum was extracted weekly from each one of the animals in both groups. The serums from each group and date were mixed in order to obtained a homogenous serum (pool) represented by equal volumes of each individual in the group. The serums were analyzed by means of ELISA. To that end, the wells were coated with 10 ng of CVLPs-pVP2-456. The tests were conducted according to a previously disclosed protocol (Current Protocols in Immunology. Edited by: Bierer, Coligan, Margulies, Shevach, Strober, John Wiley & Sons). The obtained results show that a single immunization in the absence of an adjuvant causes a potent response to the pVP2-456 protein. Similar results were obtained when other CVLP-pVP2s* obtained in Example 1 were tested. Similar results were also obtained when other both chimeric (CVLPs) and non-chimeric VLPs containing IBDV VP2 disclosed in Spanish patent applications P200300751, P200400120 and P200400121, were tested.

EXAMPLE 3

Obtaining CVLP-pVP2s* (pVP2*-BT) in Yeasts

The expression plasmid pESCURA/pVP2-456-BT was generated with the heterologous gene encoding for the FMVD chimeric peptide called BT (Zhang, Q. et al., 2002, Acta Virologica 46(1):1-9) bound to the N-temminal end of pVP2-456 for the purpose of studying the possibility of obtaining IBDV CVLP-pVP2s* in yeast (S. cerevisiae) cultures. Said chimeric BT peptide comprises the B cell epitope (located between positions 133-159 of the FMDV serotype C Spanish isolate VP1 protein) and the T cell epitope (located between positions 20-34 of the FMDV serotype Asia VP4 protein). The amino acid sequence of the B cell epitope is SIINNYMQQYQNSM (SEQ ID NO:14), whereas the amino acid sequence of the T cell epitope is MTTTYTASARGD-LAHLTTTHARHLP.

The first step in the expression plasmid construct was carried out by means of cloning the encoding region of the pVP2-456 protein into the vector pESCURAinv. The plasmid pESCURAinv was generated by means of digesting the vector pRS426 (Stratagene) with the enzyme PvuII and religating the digestion mixture. The resulting vector, pESCURA-inv, contains the region of multiple cloning in a reversed position with respect to the parental vector pRS426. The DNA fragment corresponding to the pVP2-456 protein was obtained by means of PCR with the corresponding oligonucleotides (Table 1) using the plasmid pVOTE.2/Poly as a mold (Fernández-Arias, A., Risco, C., Martínez, S., Albar, J. P. & Rodríguez, J. F. (1998). Expression of ORF A1 of infectious bursal disease virus results in the formation of virus-like particles. Journal of General Virology 79, 1047-1054). The fragment was purified, subjected to digestion with the enzymes BglII and HindIII and cloned into the vector pES-CURA.inv previously digested with the enzymes BamHI and HindIII. The resulting plasmid was called pESCURA/pVP2-456.

A DNA fragment containing the open reading frame corresponding to said FMDV chimeric BT peptide was cloned into the plasmid pESCURA/pVP2-456 previously digested with the suitable restriction enzymes. The resulting plasmid was called pESCURA/pVP2-456-BT and contains the ORFs of the IBDV pVP2-456 protein and of the FMDV chimeric BT peptide.

Said plasmid pESCURA/pVP2-456-BT was subsequently used to transform a culture of the *S. cerevisiae* yeast haploid strain 499 according to a previously disclosed protocol (Gietz, R. D. and R. A. Woods. (2002) Transformation of yeast by the Liac/SS carrier DNA/PEG method. Methods in Enzymology 350: 87-96). The yeasts transformed with the plasmid were selected by means of growth in dishes with SC medium (CSM+YNB, 2% glucose and bacto agar) supplemented with the amino acids tryptophane, leucine and histidine and lacking uracyl (-Ura). After 48 hours of incubation at 30° C., a colony was selected that was used to conduct the subsequent analyses of protein expression and the formation of CVLPs-pVP2-456-BT.

Analysis of pVP2-456 and BT protein expression and CVLP formation was conducted following a previously disclosed protocol for characterizing IBDV VLPs in other expression systems (Fernández-Arias, A., Risco, C., Martínez, S., Albar, J. P. & Rodríguez, J. F. (1998). Expression of ORF A1 of infectious bursal disease virus results in the formation of virus-like particles. *Journal of General Virology* 79, 1047-1054; Lombardo, E., Maraver, A., Castón, J. R., Rivera, J., Fernández-Arias, A., Serrano, A., Carrascosa, J. L. & Rodríguez, J. F. (1999). VP1, the putative RNA-dependent RNA polymerase of infectious bursal disease virus, forms complexes with the capsid protein VP3, leading to efficient encapsidation into virus-like particles. *Journal of Virology* 73, 6973-698). The selected colony was cultured in CSM (-Ura)+YNB liquid medium supplemented with 2% raffinose. The culture was incubated at 30° C. for 24 hours. This culture was used to inoculate, at an optical density (OD) of 0.2, a 200 ml flask of CSM (-Ura)+YNB medium supplemented with 2% galactose inducer. The culture was maintained at 30° C. for 18 hours (up to an OD between 1.0 and 2.0). The yeasts were centrifuged at 3,000 rpm, 5 minutes at 4° C., were washed with distilled water once, and the pellet was resuspended in lysis buffer (TEN: 10 mM Tris, pH 8.0; 150 mM NaCl; 1 mM EDTA)+protease inhibitors 2× (Compl Roche). One volume of glass beads with an approximate size of 425-600 microns (Sigma) was added for lysis. This mixture was subjected to a vigorous vortex for 30 seconds 4 times, with 30 second intervals, and all at 4° C. Then the soluble fraction was recovered by centrifuging the lysis mixture at 13,000 rpm for 15 minutes at 4° C. This sample was subjected to fractionation in a sucrose gradient according to the previously disclosed protocol (Lombardo, E., Maraver, A., Castón, J. R., Rivera, J., Fernández-Arias, A., Serrano, A., Carrascosa, J. L. & Rodríguez, J. F. (1999). VP1, the putative RNA-dependent RNA polymerase of infectious bursal disease virus, forms complexes with the capsid protein VP3, leading to efficient encapsidation into virus-like particles. *Journal of Virology* 73, 6973-6983). The samples obtained after fractionation and a sample of the starting material were analyzed by means of sodium dodecyl sulfate polyacrylamide gel electrophoresis (SDS-PAGE) [Current Protocols in Molecular Biology] and Western blot immunodetection using anti-pVP2-456 and anti-BT serums [Current Protocols in Molecular Biology]. The Western blot showed the presence of bands, with the predicted molecular mass corresponding to the pVP2 (48 kDa) and BT proteins (FIG. 11). These results show the correct expression of both peptides in the *S. cerevisiae* culture transformed with the plasmid pESCURA/pVP2-456-BT. Then the different gradient fractions were analyzed by means of TEM as previously described (Lombardo, E., Maraver, A., Castón, J. R., Rivera, J., Fernández-Arias, A., Serrano, A., Carrascosa, J. L. & Rodríguez, J. F. (1999). VP1, the putative RNA-dependent RNA polymerase of infectious bursal disease virus, forms complexes with the capsid protein VP3, leading to efficient encapsidation into virus-like particles. *Journal of Virology* 73: 6973-6983). TEM analysis of the gradient fractions showed the existence of CVLPs-VP2-456-BT (data not shown).

SEQUENCE LISTING

<160> NUMBER OF SEQ ID NOS: 15

<210> SEQ ID NO 1
<211> LENGTH: 13
<212> TYPE: PRT
<213> ORGANISM: Artificial Sequence
<220> FEATURE:
<223> OTHER INFORMATION: synthetic peptide

<400> SEQUENCE: 1

Phe Gly Phe Lys Asp Ile Ile Arg Ala Ile Arg Arg Ile
1               5                   10

<210> SEQ ID NO 2
<211> LENGTH: 10
<212> TYPE: PRT
<213> ORGANISM: Artificial Sequence
<220> FEATURE:
<223> OTHER INFORMATION: synthetic peptide

<400> SEQUENCE: 2

Gly Phe Lys Asp Ile Ile Arg Ala Ile Arg
1               5                   10

<210> SEQ ID NO 3
<211> LENGTH: 35
<212> TYPE: DNA
<213> ORGANISM: Artificial Sequence
<220> FEATURE:
<223> OTHER INFORMATION: oligonucleotide primer 5-VP2

<400> SEQUENCE: 3
gcgcagatct atgacaaacc tgtcagatca aaccc          35

<210> SEQ ID NO 4
<211> LENGTH: 34
<212> TYPE: DNA
<213> ORGANISM: Artificial Sequence
<220> FEATURE:
<223> OTHER INFORMATION: oligonucleotide primer NotI-441

<400> SEQUENCE: 4
gcgcgcggcc gcttatgctc ctgcaatctt cagg           34

<210> SEQ ID NO 5
<211> LENGTH: 32
<212> TYPE: DNA
<213> ORGANISM: Artificial Sequence
<220> FEATURE:
<223> OTHER INFORMATION: oligonucleotide primer HindIII-456

<400> SEQUENCE: 5
gcgcaagctt acacagctat cctccttatg gc             32

<210> SEQ ID NO 6
<211> LENGTH: 31
<212> TYPE: DNA
<213> ORGANISM: Artificial Sequence
<220> FEATURE:
<223> OTHER INFORMATION: oligonucleotide primer HindIII-466

<400> SEQUENCE: 6
gcgcaagctt aggcaggtgg aacaatgtg g               31

<210> SEQ ID NO 7
<211> LENGTH: 33
<212> TYPE: DNA
<213> ORGANISM: Artificial Sequence
<220> FEATURE:
<223> OTHER INFORMATION: oligonucleotide primer HindIII-476

<400> SEQUENCE: 7
gcgcaagctt aaccttcccc aattgcatgg ggc            33

<210> SEQ ID NO 8
<211> LENGTH: 33
<212> TYPE: DNA
<213> ORGANISM: Artificial Sequence
<220> FEATURE:
<223> OTHER INFORMATION: oligonucleotide primer HindIII-487

<400> SEQUENCE: 8
gcgcaagctt aggcctgggc tcatcgccc agc             33

<210> SEQ ID NO 9
<211> LENGTH: 32
<212> TYPE: DNA
<213> ORGANISM: Artificial Sequence
<220> FEATURE:

```
<223> OTHER INFORMATION: oligonucleotide primer HindIII-494

<400> SEQUENCE: 9
gcgcaagctt aggctcgagc agttcctgaa gc                                    32

<210> SEQ ID NO 10
<211> LENGTH: 32
<212> TYPE: DNA
<213> ORGANISM: Artificial Sequence
<220> FEATURE:
<223> OTHER INFORMATION: oligonucleotide primer HindIII-501

<400> SEQUENCE: 10
gcgcaagctt aagctcttgc ttttcctgac gc                                    32

<210> SEQ ID NO 11
<211> LENGTH: 34
<212> TYPE: DNA
<213> ORGANISM: Artificial Sequence
<220> FEATURE:
<223> OTHER INFORMATION: oligonucleotide primer HindIII-512

<400> SEQUENCE: 11
gcgcaagctt aggcgagagt cagctgcctt atgc                                  34

<210> SEQ ID NO 12
<211> LENGTH: 28
<212> TYPE: PRT
<213> ORGANISM: Artificial Sequence
<220> FEATURE:
<223> OTHER INFORMATION: synthetic peptide tag

<400> SEQUENCE: 12

Met Ser Tyr Tyr His His His His His His Asp Tyr Asp Ile Pro Thr
1               5                   10                  15

Thr Glu Asn Leu Tyr Phe Gln Gly Ala Met Gly Ser
            20                  25

<210> SEQ ID NO 13
<211> LENGTH: 10
<212> TYPE: PRT
<213> ORGANISM: Artificial Sequence
<220> FEATURE:
<223> OTHER INFORMATION: synthetic peptide

<400> SEQUENCE: 13

Glu Phe Arg Asp Ile Ile Asp Ala Thr Arg
1               5                   10

<210> SEQ ID NO 14
<211> LENGTH: 15
<212> TYPE: PRT
<213> ORGANISM: Artificial Sequence
<220> FEATURE:
<223> OTHER INFORMATION: synthetic peptide B cell epitope

<400> SEQUENCE: 14

Ser Ile Ile Asn Asn Tyr Tyr Met Gln Gln Tyr Gln Asn Ser Met
1               5                   10                  15

<210> SEQ ID NO 15
<211> LENGTH: 25
<212> TYPE: PRT
<213> ORGANISM: Artificial Sequence
<220> FEATURE:
<223> OTHER INFORMATION: synthetic peptide T cell epitope
```

```
<400> SEQUENCE: 15

Met Thr Thr Thr Tyr Thr Ala Ser Ala Arg Gly Asp Leu Ala His Leu
1               5                   10                  15

Thr Thr Thr His Ala Arg His Leu Pro
            20                  25
```

The invention claimed is:

1. A fusion protein capable of forming a virus-like particle, comprising a region A, wherein said region A consists of a pVP2 protein of infectious bursal disease virus (IBDV), or a fragment thereof, wherein said fragment comprises residues 1-441 of said pVP2 protein, and a region B comprising a heterologous polypeptide, wherein said heterologous polypeptide is not a native IBDV polypeptide and said heterologous polypeptide is useful in vaccination, therapy or diagnosis, and wherein said region B is bound to a terminal region of said region A.

2. The fusion protein of claim 1, wherein said region A consists of a fragment of said IBDV pVP2 protein selected from the group consisting of:
   (i) pVP2-441, consisting of the amino acid sequence between residue 1 and residue 441 of SEQ ID NO: 16;
   (ii) pVP2-452, consisting of the amino acid sequence between residue 1 and residue 452 of SEQ ID NO: 16;
   (iii) pVP2-456, consisting of the amino acid sequence between residue 1 and residue 456 of SEQ ID NO: 16;
   (iv) pVP2-466, consisting of the amino acid sequence between residue 1 and residue 466 of SEQ ID NO: 16;
   (v) pVP2-476, consisting of the amino acid sequence between residue 1 and residue 476 of SEQ ID NO: 16;
   (vi) pVP2-487, consisting of the amino acid sequence between residue 1 and residue 487 of SEQ ID NO: 16;
   (vii) pVP2-494, consisting of the amino acid sequence between residue 1 and residue 494 of SEQ ID NO: 16; and
   (viii) pVP2-501, consisting of the amino acid sequence between residue 1 and residue 501 of SEQ ID NO: 16.

3. The fusion protein of claim 1, wherein said region B is bound to the amino-terminal region of said region A.

4. The fusion protein of claim 1, wherein said region B is bound to the carboxyl-terminal region of said region A.

5. The fusion protein of claim 1, wherein said region B comprises a single polypeptide of interest.

6. The fusion protein of claim 1, wherein said region B comprises two or more polypeptides of interest.

7. The fusion protein of claim 1, wherein said fusion protein comprises a region A and a single region B.

8. The fusion protein of claim 1, wherein said fusion protein comprises a region A bound to a first region B and a second region B, the first region B being bound to the amino-terminal region of the region A, and the second region B being bound to the carboxyl-terminal region of the region A.

9. The fusion protein of claim 8, wherein said first region B and said second region B comprise polypeptides that are identical or different.

10. The fusion protein of claim 1, wherein said fusion protein further comprises a linker polypeptide located between said regions A and B.

11. A chimeric viral-like particle comprising at least one fusion protein of claim 1.

12. A method for producing the chimeric viral-like particle of claim 11, comprising culturing a host cell comprising a nucleic acid that encodes said fusion protein.

13. The method of claim 12, wherein said host cell is an insect cell.

14. The method of claim 12, wherein said host cell is a yeast cell.

15. A pharmaceutical composition comprising the chimeric viral-like particle of claim 11 and a pharmaceutically acceptable adjuvant or vehicle.

16. The pharmaceutical composition of claim 15, wherein said pharmaceutical composition is a vaccine.

17. A vaccine comprising a therapeutically effective amount of the chimeric viral-like particle of claim 11.

18. The method of claim 12, further comprising recovering said chimeric viral-like particle.

19. The method of claim 13, wherein the insect cell is infected with a recombinant baculovirus comprising a nucleic acid that encodes said fusion protein.

20. The fusion protein of claim 1, wherein the heterologous polypeptide comprises an epitope or antigenic determinant capable of inducing an immune response against a disease.

21. The fusion protein of claim 20, wherein the disease is caused by a microorganism.

22. The fusion protein of claim 21, wherein the microorganism is a virus, bacterium or parasite.

23. The fusion protein of claim 20, wherein the disease is a tumor.

24. A fusion protein capable of forming a virus-like particle, comprising a region A, wherein said region A consists of a pVP2 protein or a 1-n fragment of the pVP2 protein of infectious bursal disease virus (IBDV), wherein "n" is an integer between 441 and 501, and a region B comprising a heterologous polypeptide, wherein said heterologous polypeptide is not a native IBDV polypeptide and said heterologous polypeptide is useful in vaccination, therapy or diagnosis, and wherein said region B is bound to a terminal region of said region A.

25. A fusion protein capable of forming a virus-like particle, comprising a region A, wherein said region A consists of a pVP2 protein of infectious bursal disease virus (IBDV), or a fragment thereof, wherein said fragment comprises up to 501 contiguous amino acid residues starting after amino acid one of said pVP2 protein, and a region B comprising a heterologous polypeptide, wherein said heterologous polypeptide is not a native IBDV polypeptide and said heterologous polypeptide is useful in vaccination, therapy or diagnosis, and wherein said region B is bound to a terminal region of said region A.

* * * * *

UNITED STATES PATENT AND TRADEMARK OFFICE
CERTIFICATE OF CORRECTION

PATENT NO. : 7,476,387 B2
APPLICATION NO. : 11/433847
DATED : January 13, 2009
INVENTOR(S) : Rodriguez Aguirre et al.

It is certified that error appears in the above-identified patent and that said Letters Patent is hereby corrected as shown below:

Title Pg, Item (56)
In Foreign Patent Documents:
On Page 2, line 10: "WO 02/088339" should read --WO 02/088339 A2--

In Other Publications:
On Page 2, under Coulibaly et al.: "Mar. 25, 1005" should read --Mar. 25, 2005--
On Page 2, under Birghan et al.: "Ion" should read --lon--
On Page 2, under Luckow et al.: "tranposon-mediated" should read --transposon-mediated--
On Page 2, under Maraver et al.: "Indentification" should read --Identification--
On Page 2, under Maraver et al.: "2003" should read --2003.--
On Page 2, under Martinez-Torrecuadrada et al.: "disease capsid protien" should read --disease virus capsid protein--
On Page 2, under Pous et al.: "electorn" should read --electron--
On Page 3, under Qiu et al.: "structual" should read --structural--
On Page 3, under Razzini et al.: "lipoprotien" should read --lipoprotein--
On Page 3, under Sanchez and Rodriguez: "Rodriíguez" should read --Rodríguez--
On Page 3, under Shivappa et al.: "205." should read --2005.--

In the Specification:
Column 4, line 58: "(FIG. 1B, 9C" should read --(FIG. 1B, 1C)--
Column 5, line 2: "ant" should read --and--
Column 5, line 43: "in en FIG. 4C" should read --in FIG. 4C--
Column 6, line 27: "IBVD" should read --IBDV--
Column 6, line 31: "4663DR" should read --466 3DR--
Column 13, line 49: "S. cerevisae," should read --S. cerevisiae,--
Column 17, line 2: "FB/VP2-476" should read --FB/VP2-466--
Column 17, line 3: "FBNVP2-494" should read --FB/VP2-494--
Column 17, lines 3-4: "FBNVP2-512" should read --FB/VP2-512--
Column 17, line 16: "GCGCGCGGCCGGTTATGCTCCTGCAATCTTCAGG" should read --GCGCGCGGCCGCTTATGCTCCTGCAATCTTCAGG--
Column 18, lines 63-64: "re spectively" should read --respectively--
Column 19, line 39: "Convay" should read --Conway--
Column 21, line 3: "HT-pVP2NVP2" should read --HT-pVP2/VP2--
Column 22, line 5: "V-P2" should read --VP2--
Column 23, line 18: "asses" should read --assess--
Column 23, lines 21-22: "(de 328 a 311 Å)" should read --(from 328 to 311 Å)--
Column 23, line 24: "at (302 to 294 Å)" should read --(at 302 to 294 Å)--
Column 24, line 36: "FMVD" should read --FMDV--
Column 24, line 45: "SIINNYMQQYQNSM" should read --SIINNYYMQQYQNSM--
Column 24, line 47: "LAHLTTTHARHLP" should read --LAHLTTTHARHLP (SEQ ID NO: 15).--
Column 25, line 34: "6973-698)." should read --6973-6983).--

CERTIFICATE OF CORRECTION (continued)
U.S. Pat. No. 7,476,387 B2

In the Sequence Listing:
    Line 1: "<160> NUMBER OF SEQ ID NOS: 15" should read --<160> NUMBER OF SEQ ID NOS: 16--
    Add SEQ ID NO: 16:

<210> 16
<211> 1012
<212> PRT
<213> Infectious Bursal Disease Virus (IBDV)

<400> 16

Met Thr Asn Leu Ser Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
            35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
            85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
            115                 120                 125

Phe Gln Gly Ser Leu Ser Glu Leu Thr Asp Val Ser Tyr Asn Gly Leu
            130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
            165                 170                 175

Tyr Val Arg Leu Gly Asp Pro Ile Pro Ala Ile Gly Leu Asp Pro Lys

```
                  180                   185                    190
    Met Val Ala Thr Cys Asp Ser Ser Asp Arg Pro Arg Val Tyr Thr Ile
              195                   200                   205

Thr Ala Ala Asp Asp Tyr Gln Phe Ser Ser Gln Tyr Gln Pro Gly Gly
          210                   215                   220

Val Thr Ile Thr Leu Phe Ser Ala Asn Ile Asp Ala Ile Thr Ser Leu
    225                   230                   235                   240

Ser Val Gly Gly Glu Leu Val Phe Arg Thr Ser Val His Gly Leu Val
                  245                   250                   255

Leu Gly Ala Thr Ile Tyr Leu Ile Gly Phe Asp Gly Thr Thr Val Ile
              260                   265                   270

Thr Arg Ala Val Ala Ala Asn Asn Gly Leu Thr Thr Gly Thr Asp Asn
          275                   280                   285

Leu Met Pro Phe Asn Leu Val Ile Pro Thr Asn Glu Ile Thr Gln Pro
            290                   295                   300

Ile Thr Ser Ile Lys Leu Glu Ile Val Thr Ser Lys Ser Gly Gly Gln
    305                   310                   315                   320

Ala Gly Asp Gln Met Ser Trp Ser Ala Arg Gly Ser Leu Ala Val Thr
                  325                   330                   335

Ile His Gly Gly Asn Tyr Pro Gly Ala Leu Arg Pro Val Thr Leu Val
              340                   345                   350

Ala Tyr Glu Arg Val Ala Thr Gly Ser Val Val Thr Val Ala Gly Val
            355                   360                   365

Ser Asn Phe Glu Leu Ile Pro Asn Pro Glu Leu Ala Lys Asn Leu Val
        370                   375                   380
```

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
          405                 410                 415

Arg Glu Tyr Thr Asp Phe Arg Glu Tyr Phe Met Glu Val Ala Asp Leu
          420                 425                 430

Asn Ser Pro Leu Lys Ile Ala Gly Ala Phe Gly Phe Lys Asp Ile Ile
          435                 440                 445

Arg Ala Ile Arg Arg Ile Ala Val Pro Val Val Ser Thr Leu Phe Pro
          450                 455                 460

Pro Ala Ala Pro Leu Ala His Ala Ile Gly Glu Gly Val Asp Tyr Leu
465                 470                 475                 480

Leu Gly Asp Glu Ala Gln Ala Ala Ser Gly Thr Ala Arg Ala Ala Ser
          485                 490                 495

Gly Lys Ala Arg Ala Ala Ser Gly Arg Ile Arg Gln Leu Thr Leu Ala
          500                 505                 510

Ala Asp Lys Gly Tyr Glu Val Val Ala Asn Leu Phe Gln Val Pro Gln
          515                 520                 525

Asn Pro Val Val Asp Gly Ile Leu Ala Ser Pro Gly Val Leu Arg Gly
          530                 535                 540

Ala His Asn Leu Asp Cys Val Leu Arg Glu Gly Ala Thr Leu Phe Pro
545                 550                 555                 560

Val Val Ile Thr Thr Val Glu Asp Ala Met Thr Pro Lys Ala Leu Asn
          565                 570                 575

Ser Lys Met Phe Ala Val Ile Glu Gly Val Arg Glu Asp Leu Gln Pro
          580                 585                 590

Pro Ser Gln Arg Gly Ser Phe Ile Arg Thr Leu Ser Gly His Arg Val
　　　595　　　　　　　　600　　　　　　　　605

Tyr Gly Tyr Ala Pro Asp Gly Val Leu Pro Leu Glu Thr Gly Arg Asp
　　610　　　　　　　　615　　　　　　　　620

Tyr Thr Val Val Pro Ile Asp Asp Val Trp Asp Asp Ser Ile Met Leu
625　　　　　　　　630　　　　　　　635　　　　　　　　640

Ser Lys Asp Pro Ile Pro Pro Ile Val Gly Asn Ser Gly Asn Leu Ala
　　　　　　645　　　　　　　　650　　　　　　　　655

Ile Ala Tyr Met Asp Val Phe Arg Pro Lys Val Pro Ile His Val Ala
　　　　660　　　　　　　　665　　　　　　　　670

Met Thr Gly Ala Leu Asn Ala Cys Gly Glu Ile Glu Lys Val Ser Phe
　　　675　　　　　　　　680　　　　　　　685

Arg Ser Thr Lys Leu Ala Thr Ala His Arg Leu Gly Leu Arg Leu Ala
　　690　　　　　　　　695　　　　　　　　700

Gly Pro Gly Ala Phe Asp Val Asn Thr Gly Pro Asn Trp Ala Thr Phe
705　　　　　　　　710　　　　　　　715　　　　　　　　720

Ile Lys Arg Phe Pro His Asn Pro Arg Asp Trp Asp Arg Leu Pro Tyr
　　　　　　725　　　　　　　　730　　　　　　　735

Leu Asn Leu Pro Tyr Leu Pro Pro Asn Ala Gly Arg Gln Tyr His Leu
　　　　　740　　　　　　　745　　　　　　　　750

Ala Met Ala Ala Ser Glu Phe Lys Glu Thr Pro Glu Leu Glu Ser Ala
　　　755　　　　　　　　760　　　　　　　765

Val Arg Ala Met Glu Ala Ala Ala Asn Val Asp Pro Leu Phe Gln Ser
　　770　　　　　　　　775　　　　　　　　780

Ala Leu Ser Val Phe Met Trp Leu Glu Glu Asn Gly Ile Val Thr Asp

|   785              |   790              |   795              |   800              |

Met Ala Asn Phe Ala Leu Ser Asp Pro Asn Ala His Arg Met Arg Asn
          805                  810                815

Phe Leu Ala Asn Ala Pro Gln Ala Gly Ser Lys Ser Gln Arg Ala Lys
          820                  825                830

Tyr Gly Thr Ala Gly Tyr Gly Val Glu Ala Arg Gly Pro Thr Pro Glu
          835                  840                845

Glu Ala Gln Arg Glu Lys Asp Thr Arg Ile Ser Lys Lys Met Glu Thr
          850                  855                860

Met Gly Ile Tyr Phe Ala Thr Pro Glu Trp Val Ala Leu Asn Gly His
865                  870                  875                880

Arg Gly Pro Ser Pro Gly Gln Val Lys Tyr Trp Gln Asn Lys Arg Glu
          885                  890                895

Ile Pro Asp Pro Asn Glu Asp Tyr Leu Asp Tyr Val His Ala Glu Lys
          900                  905                910

Ser Arg Leu Ala Ser Glu Glu Gln Ile Leu Arg Ala Ala Thr Ser Ile
          915                  920                925

Tyr Gly Ala Pro Gly Gln Ala Glu Pro Pro Gln Ala Phe Ile Asp Glu
          930                  935                940

Val Ala Lys Val Tyr Glu Ile Asn His Gly Arg Gly Pro Asn Gln Glu
945                  950                  955                960

Gln Met Lys Asp Leu Leu Leu Thr Ala Met Glu Met Lys His Arg Asn
          965                  970                975

Pro Arg Arg Ala Leu Pro Lys Pro Lys Pro Lys Pro Asn Ala Pro Thr
          980                  985                990

Gln Arg Pro Pro Gly Arg Leu Gly Arg Trp Ile Arg Thr Val Ser Asp
          995                  1000              1005

Glu Asp Leu Glu
    1010

CERTIFICATE OF CORRECTION (continued)
U.S. Pat. No. 7,476,387 B2

In the Claims:
Claim 2, column 31, line 39: "SEQID" should read --SEQ ID--

Signed and Sealed this

Sixth Day of April, 2010

David J. Kappos
*Director of the United States Patent and Trademark Office*